(12) United States Patent
Higgins et al.

(10) Patent No.: US 11,833,022 B2
(45) Date of Patent: Dec. 5, 2023

(54) INCONTINENCE CLAMPING DEVICE

(71) Applicants: Shawn P. Higgins, Huizhou (CN); Ignacio Navarro De Corcuera, Larnaca (CY)

(72) Inventors: Shawn P. Higgins, Huizhou (CN); Ignacio Navarro De Corcuera, Larnaca (CY)

(73) Assignee: Cross Innovations, LLC, Cheyenne, WY (US)

( * ) Notice: Subject to any disclaimer, the term of this patent is extended or adjusted under 35 U.S.C. 154(b) by 0 days.

(21) Appl. No.: 18/113,261

(22) Filed: Feb. 23, 2023

(65) Prior Publication Data

US 2023/0190438 A1 Jun. 22, 2023

Related U.S. Application Data

(63) Continuation of application No. 18/083,631, filed on Dec. 19, 2022, which is a continuation-in-part of application No. 17/063,804, filed on Oct. 6, 2020.

(51) Int. Cl.
*A61F 2/00* (2006.01)

(52) U.S. Cl.
CPC .................. *A61F 2/0054* (2013.01)

(58) Field of Classification Search
CPC .... A61F 2/0054; A61F 2/0045; A61F 2/0031; A61F 2/0018; A61F 2/0013; A61F 2/0009; A61F 2/0004; A61F 2/00
See application file for complete search history.

(56) References Cited

U.S. PATENT DOCUMENTS

| | | | |
|---|---|---|---|
| 4,942,886 A | 7/1990 | Timmons | |
| 5,571,125 A * | 11/1996 | Chadwick | A61B 17/122 606/151 |
| 6,131,576 A * | 10/2000 | Davis | A61F 2/0054 128/885 |
| D447,564 S | 9/2001 | Stewart, Jr. | |
| 6,843,253 B2 | 1/2005 | Parkes | |
| 7,107,995 B2 * | 9/2006 | Parkes | A61F 5/41 600/38 |
| D659,827 S | 5/2012 | Stringham et al. | |
| 10,624,728 B2 * | 4/2020 | Velez Wiesner | A61F 2/0054 |
| D896,961 S | 9/2020 | Mesa | |

(Continued)

FOREIGN PATENT DOCUMENTS

WO  WO-2019063994 A1 *  4/2019

OTHER PUBLICATIONS

Confidence Clamp by Lunderg, https://www.amazon.com/dp/B081N6ZSGV, sold on or about Nov. 17, 2019.

(Continued)

*Primary Examiner* — Tarla R Patel
(74) *Attorney, Agent, or Firm* — Dan B Law PLLC; Daniel S. Bretzius

(57) ABSTRACT

The disclosure describes and illustrates improvements to an incontinence clamping device, to include an adjustable hinge. An embodiment of the incontinence clamping device more specifically includes two arms coupled together with a hinge pin in a way that permits two configurations of the arms. The improvements and inventions discussed herein provide a better user experience and increase the usability of the incontinence clamp device.

5 Claims, 19 Drawing Sheets

(56) References Cited

U.S. PATENT DOCUMENTS

| | | |
|---|---|---|
| D931,454 S | 9/2021 | Higgins et al. |
| 11,351,020 B2 | 7/2022 | Velez Wiesner |
| 2004/0129277 A1* | 7/2004 | Parkes ................. A61F 2/0054 |
| | | 128/885 |
| 2008/0121241 A1* | 5/2008 | Dennis ................. A61F 2/0054 |
| | | 128/885 |
| 2019/0038390 A1 | 2/2019 | Donati |
| 2019/0133739 A1 | 5/2019 | Kim |
| 2019/0269489 A1* | 9/2019 | Kuenzel ................ A61F 2/0054 |
| 2020/0197146 A1 | 6/2020 | Velez Wiesner |
| 2021/0338404 A1* | 11/2021 | Velez Wiesner ...... A61F 2/0054 |

OTHER PUBLICATIONS

Wiesner Incontinence Clamp, https://www.amazon.com/dp/B00F3HZJ74, sold on or about Sep. 10, 2013.

\* cited by examiner

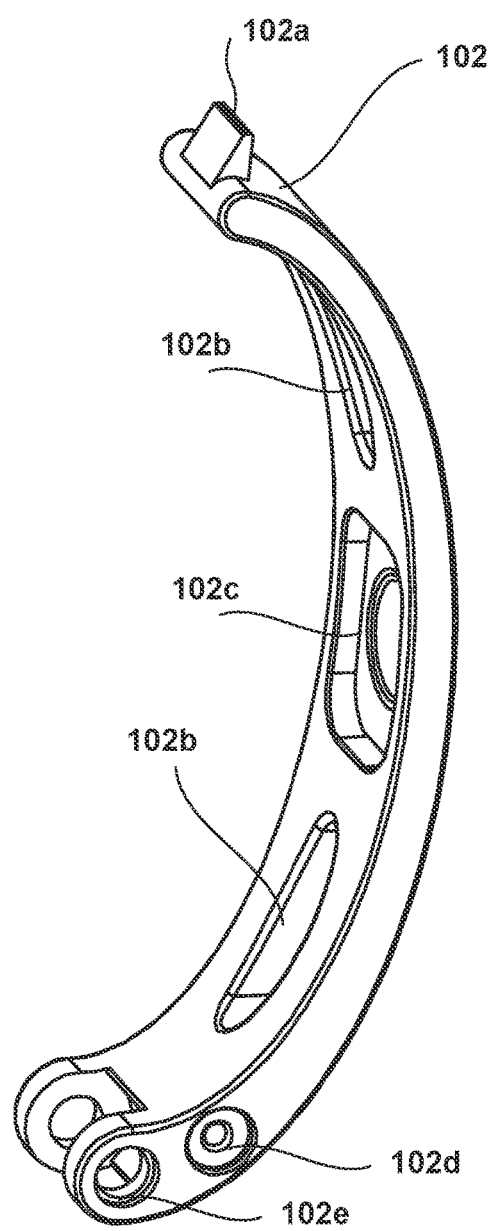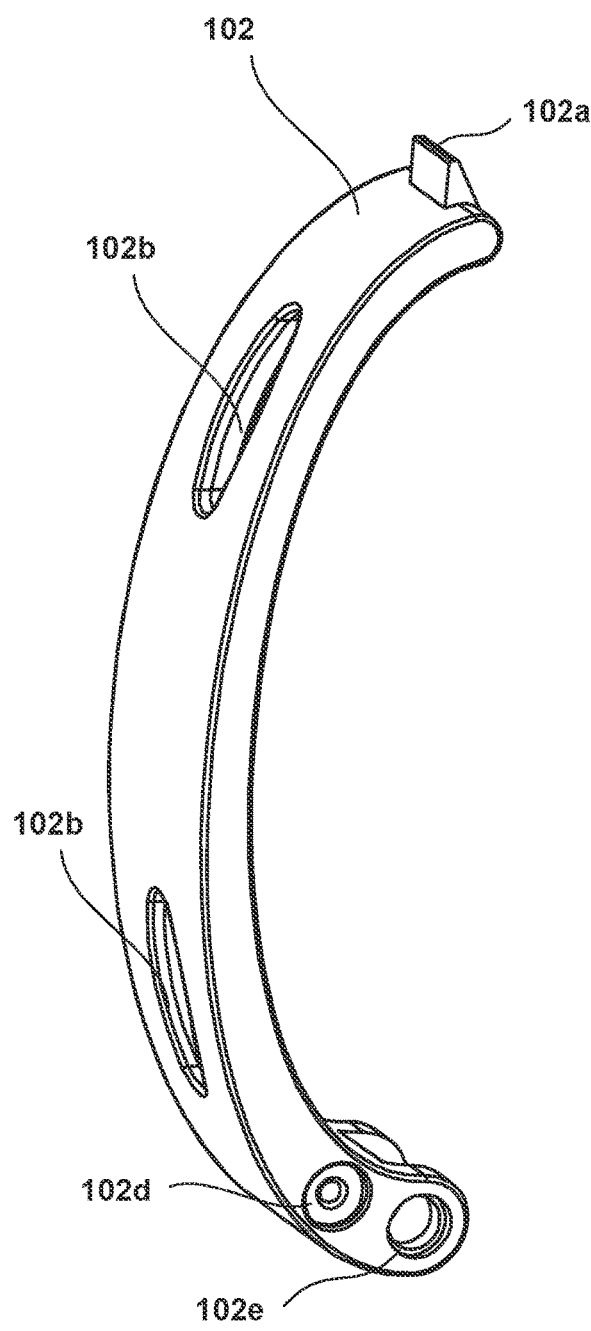
FIG. 2A
FIG. 2B

INCONTINENCE CLAMPING DEVICE

FIELD OF DISCLOSURE

The present disclosure relates to clamps used to assist users with urinary incontinence. In some embodiments, the disclosure relates to specific features of an incontinence clamp device used by males, including a user-friendly hinge configuration.

BACKGROUND

Incontinence is the uncontrolled and undesired passage of urine and is generally considered as a problem faced by many men and, especially, older men. Incontinence may be caused by, for example, medical operations, partial or full sphincter loss, disease, neurological dysfunction, malformation of the urethral valve, and physical deterioration accompanying advancing age such that the natural urethral valve or sphincter is no longer capable of controlling the flow of urine from the bladder. Whatever the cause, incontinence is a significant problem resulting in distress, embarrassment, inconvenience, and restriction of activities. To date, the common means of preventing the involuntary flow of urine in incontinent males has been to clamp the penis via a device. However, the use of such conventional device generally becomes painful, socially restrictive, and difficult to keep clean. Such devices cause pressure to be applied upon the urethra, which consequently restricts the flow of urine through the penis.

U.S. Pat. No. 7,107,995 (entitled "Urinary-control device") discloses a urinary-control device for inhibiting male incontinence includes an upper clamping member; a lower clamping member; a hinge; and a releasable, self-locking mechanism. The upper clamping member has first and second distal ends and a substantially arcuate inner surface extending therebetween. The inner surface is adapted to be disposed about a portion of a penis. The lower clamping member has first and second distal ends and a substantially arcuate inner surface extending therebetween. The inner surface is adapted to be disposed about a portion of the penis and opposite the upper clamping member. The hinge is defined at the first distal ends for allowing articulated movement of the upper and lower clamping members relative to one another. The self-locking mechanism is defined at the second distal ends opposite the hinge and adapted to adjustably lock the second distal ends together, thereby mounting the device to the penis. The lower clamping member includes a removable pressure mechanism mounted on the inner surface of the lower clamping member and between the distal ends thereof so as to be located generally opposite the urethra of the penis. The removable pressure mechanism extends in a direction toward the inner surface of the upper clamping member so as to collapse the urethra in such a manner as to inhibit flow of urine therethrough when the device is mounted to the penis.

U.S. patent Ser. No. 10/624,728 (entitled "External male incontinence clamp") discloses an incontinence clamp includes an upper clamp arm and a lower clamp arm. Each of the upper and lower clamp arms include a first end, a second end, an inner surface, and an outer surface. The inner surfaces face each other. A hinge pivotally connects the first ends of the upper and lower clamp arms together. An upper guide is coupled to the inner surface of the upper clamp arm and a lower guide is coupled to the inner surface of the lower clamp arm. A connector releasably connects the second ends of the upper clamp arm and the lower clamp arm together.

The foregoing approaches to alleviating the problem of urinary incontinence in men leave much to be desired, since these designs offer little in the way of comfort or convenience for the user. In addition, none of these clamps is capable of adjusting pressure upon the urethra. It should be obvious to the casual observer that such devices are neither comfortable nor efficient in resolving the problems imposed by an incontinent condition. Thus, there is a need for an improved penile clamp that is safe, comfortable, easily cleanable, and more socially practical (i.e., utilizing one-handed operation) than that heretofore devised.

SUMMARY

It will be understood that this disclosure is not limited to the particular incontinence clamping device described herein, as there can be multiple possible embodiments of the present disclosure which are not expressly illustrated in the present disclosure. It is also to be understood that the terminology used in the description is for the purpose of describing the particular versions or embodiments only and is not intended to limit the scope of the present disclosure.

The present disclosure describes an incontinence clamping device with a variable hinge, having two modes or configurations, to permit variability and customization of the device for user needs and preferences. The embodiments disclosed herein include an upper clamp arm and a bottom clamp arm rotatably coupled to one another with a hinge pin, the hinge pin configured to translate within an elongated opening of one arm, to permit an increasing or decreasing of distance between the arms, which changes the size and pressure of the device for the user, Additional advantages and details are also described herein with reference to the provided drawings. Some embodiments of the incontinence clamping device may incorporate only one of the improvements discussed herein, while other embodiments may include a combination of such improvements. Embodiments of the incontinence clamping device are not restricted to the examples illustrated in the drawings, as, due to the number of possible embodiments, only some embodiments can be shown in the figures.

BRIEF DESCRIPTION OF THE, DRAWINGS

The disclosure below is made with reference to the drawings, in which,

FIG. 2A is a diagram that illustrates a first perspective view of an upper clamp arm of the incontinence clamping device, according to an exemplary embodiment of the present invention;

FIG. 2B is a diagram that illustrates a second perspective view of the upper clamp arm of the incontinence clamping device, according to an exemplary embodiment of the present invention;

Figure 22:
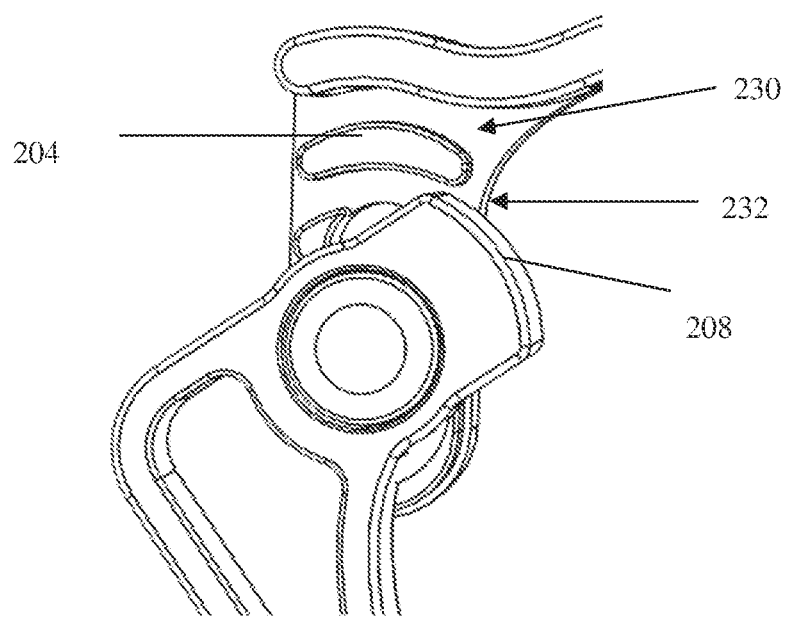
Figure 23:
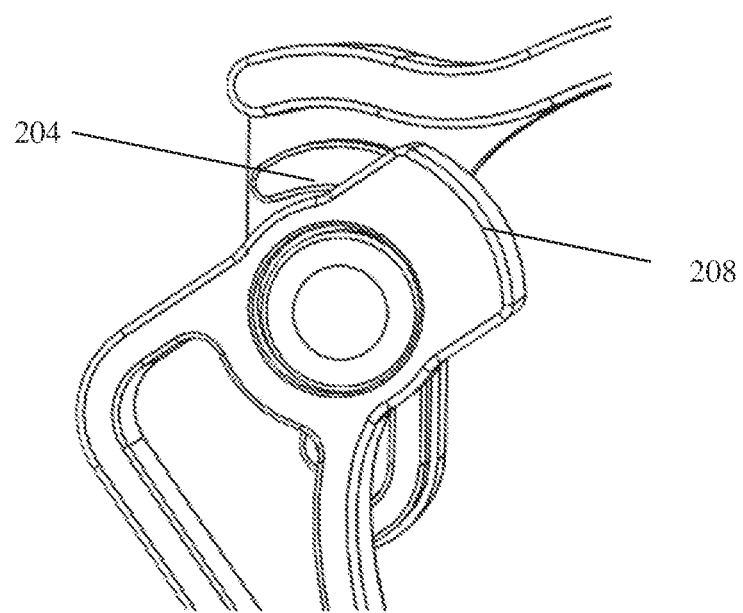

FIG. 22 is a diagram that illustrates a partial perspective close-up view of an upper clamp arm and bottom clamp arm coordinating with one another to place the incontinence clamping device in the second mode; and FIG. 23 is a diagram that illustrates a partial perspective close-up view of an upper clamp arm and bottom clamp arm coordinating with one another to place the incontinence clamping device in the first mode.

DETAILED DESCRIPTION

As used in the specification and claims, the singular forms "a", "an", and "the" may also include plural references. For example, the term "an article" may include a plurality of articles. Those with ordinary skill in the art will appreciate that the elements in the figures are illustrated for simplicity and clarity and are not necessarily drawn to scale. For example, the dimensions of some of the elements in the figures may be exaggerated, relative to other elements, to improve the understanding of the present invention. There may be additional components described in the foregoing application that are not depicted on one of the described drawings. In the event such a component is described, but not depicted in a drawing, the absence of such a drawing should not be considered as an omission of such design from the specification.

Before describing the present invention in detail, it should be observed that the present invention utilizes a combination of components, which constitutes a unique design of an easily adjustable and flexible incontinence clamping device. This device can be used for restricting the flow of urine through the penis of a human male and providing for the voluntary release of urine. Accordingly, the components have been represented, showing only specific details that are pertinent for an understanding of the present invention so as not to obscure the disclosure with details that will be readily apparent to those with ordinary skill in the art having the benefit of the description herein. As required, the detailed embodiments of the present invention are disclosed herein. However, it is to be understood that the disclosed embodiments are merely exemplary of the present invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the present invention.

References to terms "one embodiment", "an embodiment", "another embodiment", "yet another embodiment", "one example", "an example", "another example", "yet another example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in an embodiment" does not necessarily refer to the same embodiment. The words "comprising", "having", "containing", and "including", and other forms thereof, are intended to be equivalent in meaning and be open ended in that an item or items following any one of these words is not meant to be an exhaustive listing of such item or items or meant to be limited to only the listed item or items.

Unless stated otherwise, terms such as "first" and "second" are used to arbitrarily distinguish between the elements or entities. Thus, these terms are not necessarily intended to indicate temporal or other prioritization of such elements or priorities. While various exemplary embodiments of the disclosed incontinence clamping device have been described below, a person having ordinary skills in the art would understand that the incontinence clamping device have been presented for purposes of example only, and not limitations. It is not exhaustive and does not limit the present invention to the precise form disclosed. Modifications and variations of the disclosed incontinence clamping device are possible considering the below teachings or may be acquired from practicing of the present invention, without departing the breadth or scope.

The incontinence clamping device of the present invention will now be described with reference to the accompanying drawings.

Figure 1:
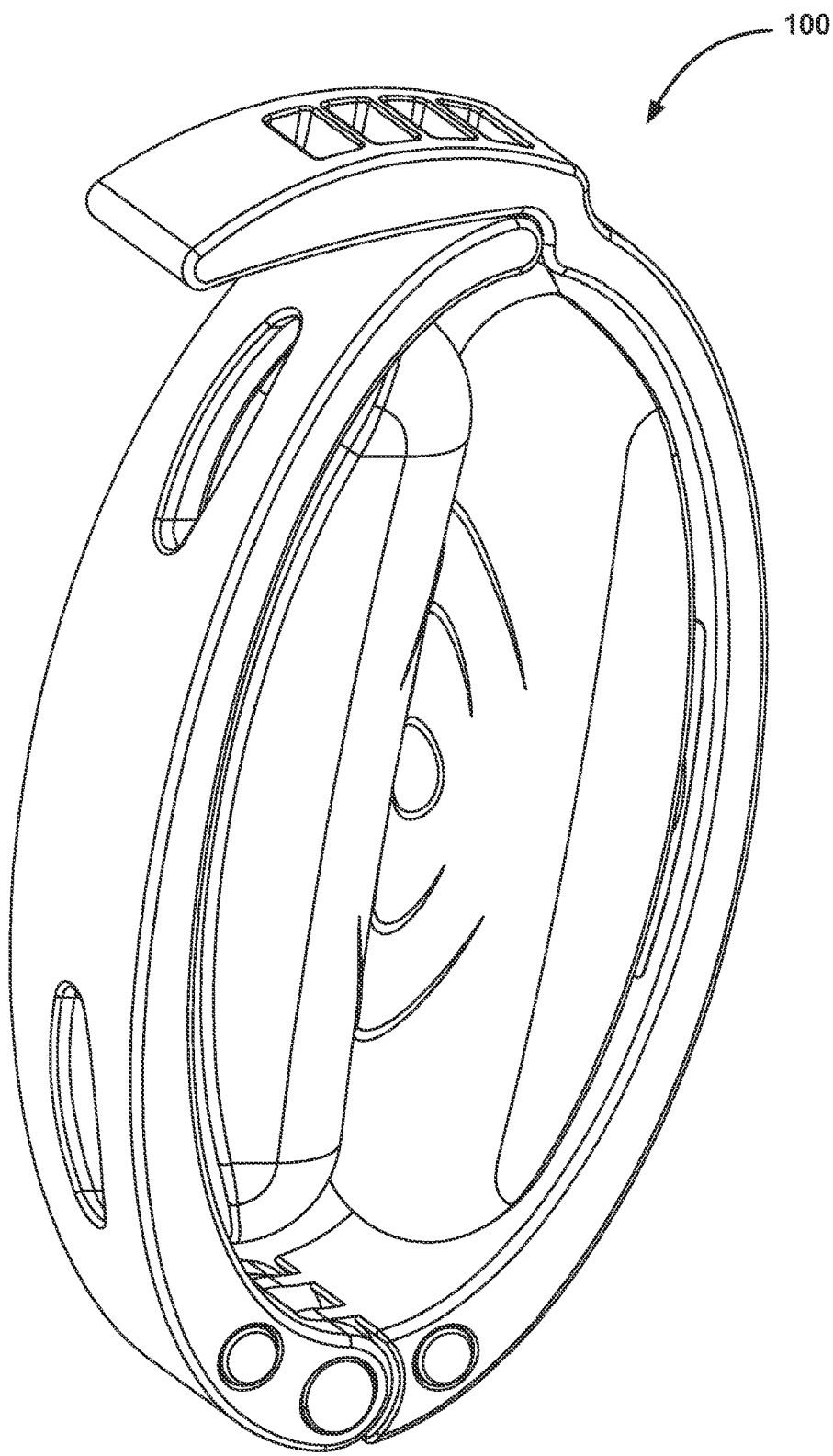
FIG. 1 is a diagram that illustrates a perspective view of an incontinence clamping device, according to an exemplary embodiment of the present invention.

FIG. 1 is a diagram that illustrates a perspective view of an incontinence clamping device 100, according to an exemplary embodiment of the present invention. The incontinence clamping device 100 may be configured to allow for delivery of different pressures to the urethra and the corpus spongiosum as a function of various sizes of penises in a flaccid state. The incontinence clamping device 100 comprises one or more variable adjustment components that are configured to enable application of different pressures to the urethra and the corpus spongiosum to accommodate needs of individual users. The incontinence clamping device 100 has been designed to permit blood flow through the penis while preventing or substantially reducing leakage from the urethra. The incontinence clamping device 100 employs a quick-release mechanism that may be utilized for easy positioning on the penile shaft and removal therefrom for urination and is more convenient and easier to attach, remove, and use. The incontinence clamping device 100 is a lightweight and compact in design and, thus, unobtrusive. The incontinence clamping device 100 uses variable adjustment to enable application of different pressures to the penis to accommodate needs of individual users. The incontinence clamping device 100 does not inflict pain, trauma, and/or damage to the skin and underlying tissues of the penile shaft. The incontinence clamping device 100 has been designed to be worn more comfortably by the user and, thus, gives the user more confidence and freedom of movement. Various components of the incontinence clamping device 100 will now be described below in conjunction with FIGS. 2-23.

FIG. 2A is a diagram that illustrates a first perspective view of an upper clamp arm 102 of the incontinence clamping device 100, according to an exemplary embodiment of the present invention. In FIG. 2A, the first perspective view of the upper clamp arm 102 has been shown from inside. FIG. 2B is a diagram that illustrates a second perspective view of the upper clamp arm 102 of the incontinence clamping device 100, according to an exemplary embodiment of the present invention. In FIG. 2B, the second perspective view of the upper clamp arm 102 has been shown from outside.

In an embodiment, the upper clamp arm 102 comprises a stopper 102a, a plurality of gaps 102b (that can be seen from inside as well as outside as shown in FIGS. 2A and 2B), and a locking segment 102c (that can be seen only from inside as shown in FIG. 2A and is not visible from outside). The locking segment 102c may be used for facilitating a locking mechanism with a lock ring (as described later in conjunction with FIGS. 7A and 7B). The upper clamp arm 102 further comprises a plug-in hole 102d and a plug-in hole 102e. These holes are used for plugging one or more plastic stoppers or screws while connecting the upper clamp arm 102 to a bottom clamp arm (shown in FIGS. 3A and 3B).

Figures 3A, 3B:
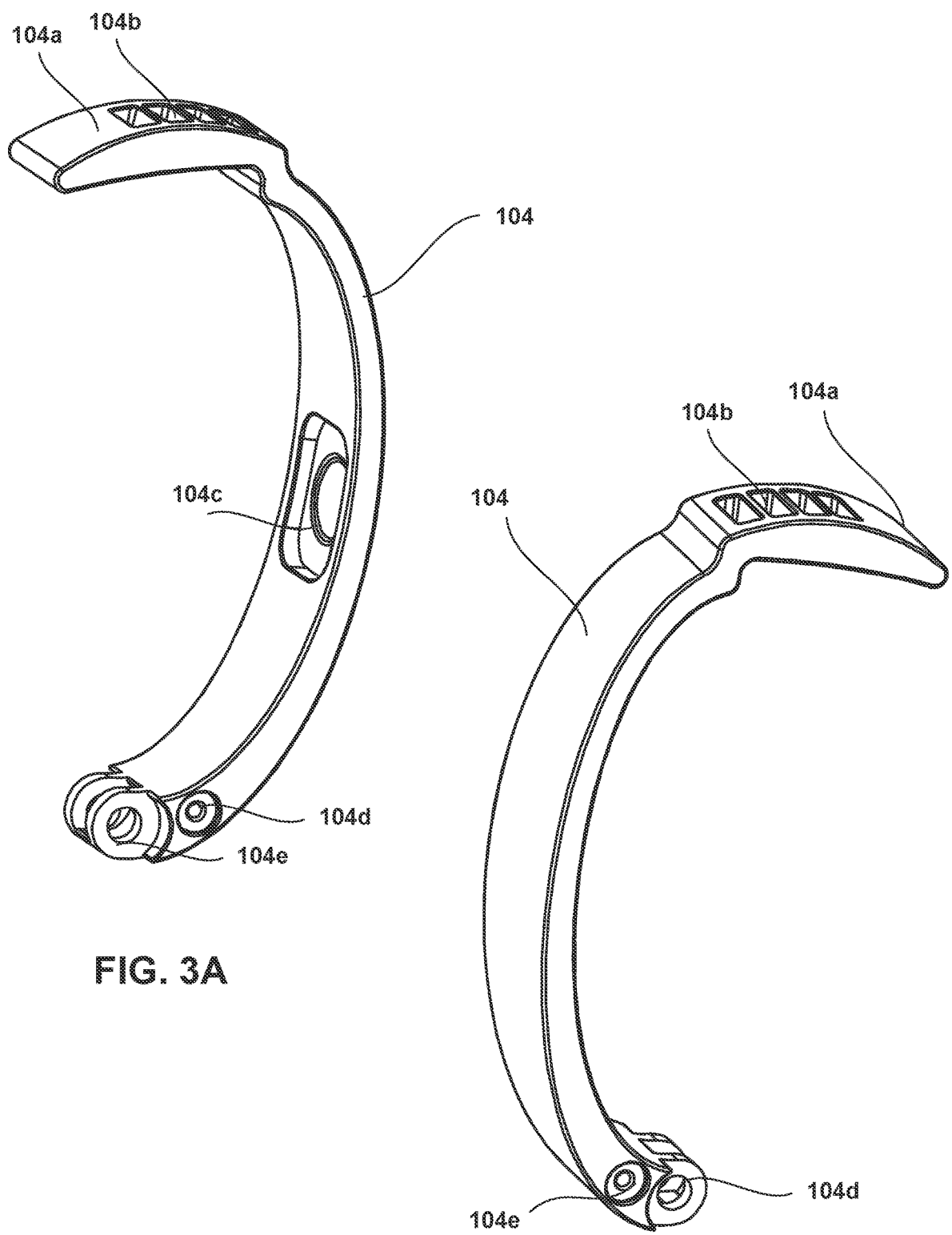
FIG. 3A is a diagram that illustrates a first perspective view of a bottom clamp arm of the incontinence clamping device, according to an exemplary embodiment of the present invention.
FIG. 3B is a diagram that illustrates a second perspective view of the bottom clamp arm of the incontinence clamping device, according to an exemplary embodiment of the present invention.

In an embodiment, the upper clamp arm 102 may be made up of a polycarbonate material. The stopper 102a may be a hook or hinge or interlocking tooth that is attached to an edge of the upper clamp arm 102 as shown in FIGS. 2A and 2B. The stopper 102a may be made up of a polycarbonate material. The stopper 102a may be secured in between a plurality of interlocking gaps, releasably connecting the one or more ends together. As illustrated in the Figures, the stopper 102a may protrude from the outer surface of the upper clamp arm 102. The plurality of interlocking gaps may protrude from a surface extending from one end of the bottom clamp arm as shown in FIGS. 3A and 3B. Pressing the clamp arms together releasably retains the second end of the upper clamp arm 102 to the second end of the bottom clamp arm. The stopper 102a disposed in between different interlocking gaps adjusts the diameter of the incontinence clamping device 100.

FIG. 3A is a diagram that illustrates a first perspective view of a bottom clamp arm 104 of the incontinence clamping device 100, according to an exemplary embodiment of the present invention. In FIG. 3A, the first perspective view of the bottom clamp arm 104 has been shown from inside. FIG. 3B is a diagram that illustrates a second perspective view of the bottom clamp arm 104 of the incontinence clamping device 100, according to an exemplary embodiment of the present invention. In FIG. 3B, the second perspective view of the bottom clamp arm 104 has been shown from outside. In an embodiment, the bottom clamp arm 104 may be made up of a polycarbonate material.

In an embodiment, the bottom clamp arm 104 comprises a device locking component 104a that includes the plurality of interlocking gaps 104b. These gaps 104b can be used along with the stopper 102a to facilitate the locking of the upper clamp arm 102 and the bottom clamp arm 104 of the incontinence clamping device 100. One of the gaps 104b may be selected to adjust the size of the incontinence clamping device 100. During the locking, the stopper 102a removably engages with one of the gaps 104b, thereby securing the upper clamp arm 102 with the bottom clamp arm 104 of the incontinence clamping device 100.

In an embodiment, the bottom clamp arm 104 further comprises a locking segment 104c (that can be seen only from inside as shown in FIG. 3A and is not visible from outside). The locking segment 104c may be used for facilitating a locking mechanism with a lock ring (as described later in conjunction with FIGS. 7A and 7B). Basically, the lock ring fits into the locking segment 104c from inside of the bottom clamp arm 104. The bottom clamp arm 104 further comprises a plug-in hole 104d and a plug-in hole 104e. These holes are used for plugging one or more plastic stoppers or screws while connecting the upper clamp arm 102 to the bottom clamp arm 104.

Figure 4A:
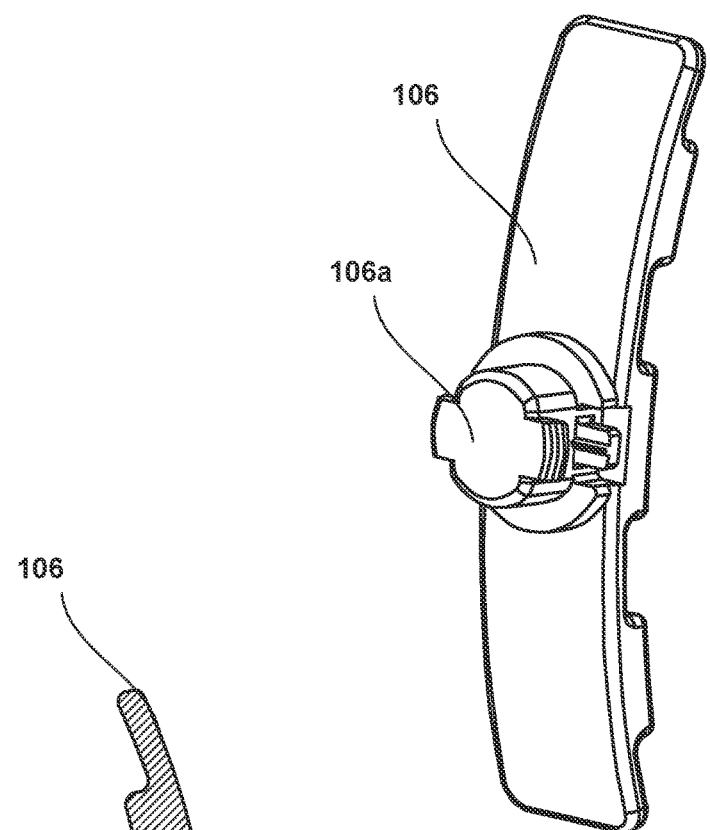
FIG. 4A is a diagram that illustrates a first perspective view of a top stabilizer of the incontinence clamping device, according to an exemplary embodiment of the present invention.
Figure 4C:
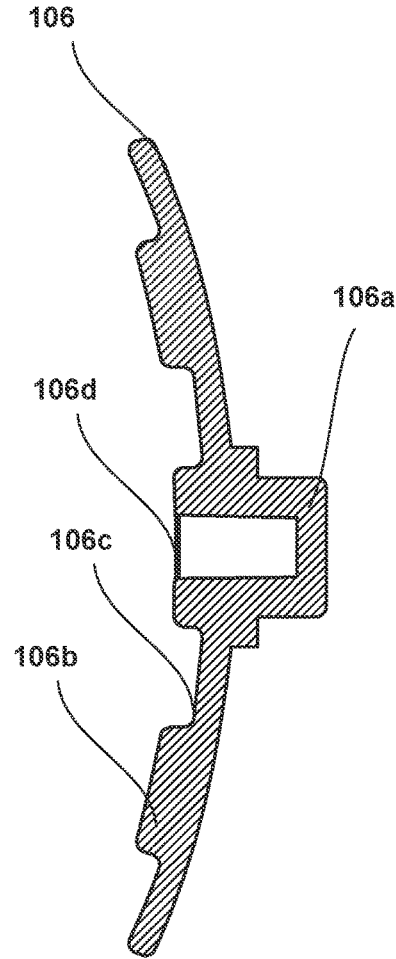
FIG. 4C is a diagram that illustrates a cross-sectional side view of the top stabilizer of the incontinence clamping device, according to an exemplary embodiment of the present invention.
Figure 4B:
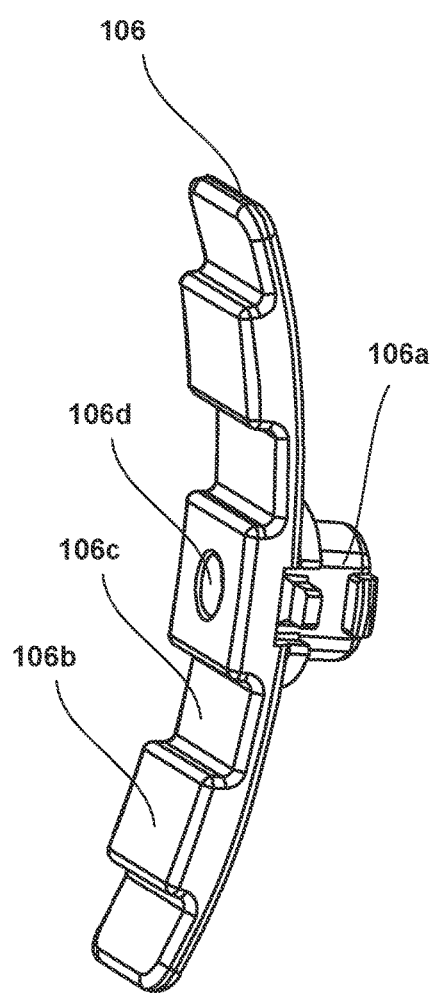
FIG. 4B is a diagram that illustrates a second perspective view of the top stabilizer of the incontinence clamping device, according to an exemplary embodiment of the present invention.

FIG. 4A is a diagram that illustrates a first perspective view of a top stabilizer 106 of the incontinence clamping device 100, according to an exemplary embodiment of the present invention. In FIG. 4A, the first perspective view of the top stabilizer 106 has been shown from outside showing an outer surface. FIG. 4B is a diagram that illustrates a second perspective view of the top stabilizer 106 of the incontinence clamping device 100, according to an exemplary embodiment of the present invention. In FIG. 4B, the second perspective view of the top stabilizer 106 has been shown from inside showing an inner surface. FIG. 4C is a diagram that illustrates a cross-sectional side view of the top stabilizer 106 of the incontinence clamping device 100, according to an exemplary embodiment of the present invention. In an embodiment, the top stabilizer 106 may be made up of a polycarbonate material.

In an embodiment, the top stabilizer 106 may comprise a lock 106a (provided on the outer surface) that is configured to get locked with the lock ring of the upper clamp arm 102. In one embodiment, the lock 106a may be manually placed into the lock ring and then may be manually rotated in one direction (for example, in a clockwise direction) to complete the locking of the lock 106a with the lock ring of the upper clamp arm 102. Similarly, to perform unlocking, the lock 106a may be manually rotated in the opposite direction (for example, in an anti-clockwise direction) to unlock the lock 106a from the lock ring of the upper clamp arm 102. In another embodiment, the lock 106a may be a toggle lock and may include a mechanical button that can be operated to lock or unlock the lock 106a into or out of the lock ring of the upper clamp arm 102.

In an embodiment, the top stabilizer 106 may further comprise the inner surface having a plurality of zig-zag portions (as shown by 106b and 106c) including one or more elevated portions 106b and non-elevated portions 106c. Further, the central elevated portion may include a circular gap or hole 106d. The elevated portions 106b and the non-elevated portions 106c may be adjacent to each other. Each of the elevated portions 106b or the non-elevated portions 106c may be square or rectangular in shape as shown.

Figure 5A:
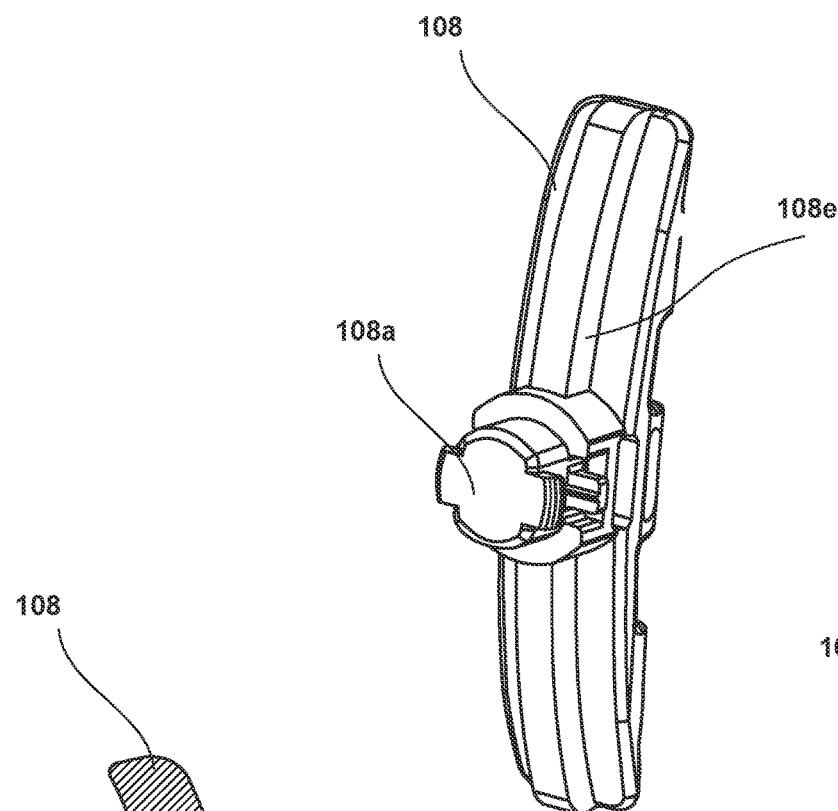
FIG. 5A is a diagram that illustrates a first perspective view of a bottom stabilizer of the incontinence clamping device, according to an exemplary embodiment of the present invention.
Figure 5C:
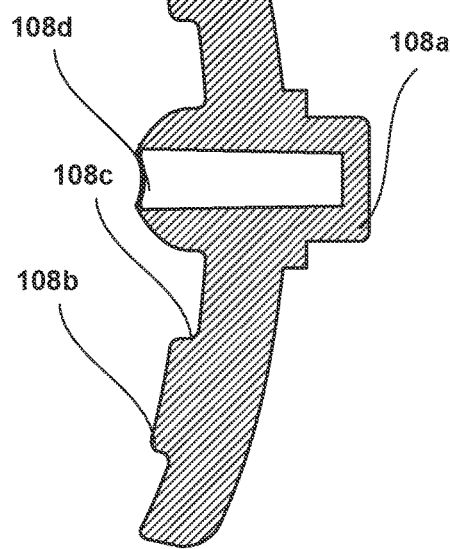
FIG. 5C is a diagram that illustrates a cross-sectional side view of the bottom stabilizer of the incontinence clamping device, according to an exemplary embodiment of the present invention.
Figure 5B:
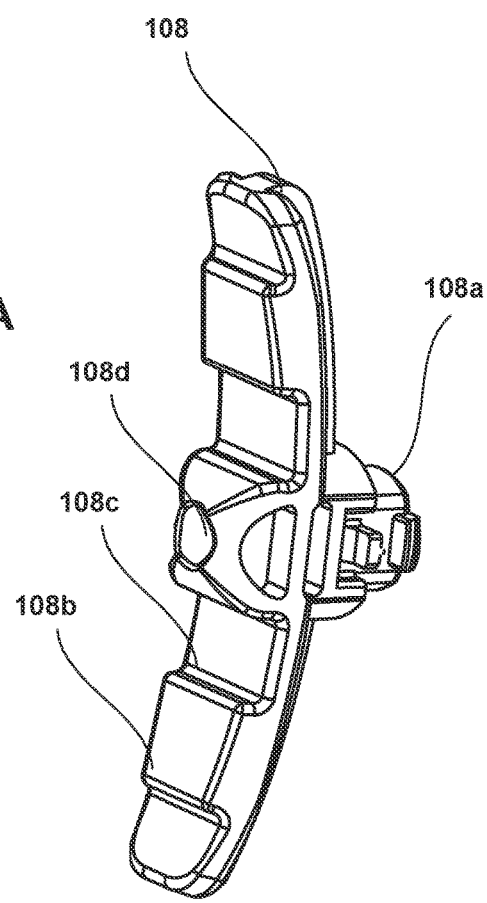
FIG. 5B is a diagram that illustrates a second perspective view of the bottom stabilizer of the incontinence clamping device, according to an exemplary embodiment of the present invention.

FIG. 5A is a diagram that illustrates a first perspective view of a bottom stabilizer 108 of the incontinence clamping device 100, according to an exemplary embodiment of the present invention. In FIG. 5A, the first perspective view of the bottom stabilizer 108 has been shown from outside showing an outer surface. FIG. 5B is a diagram that illustrates a second perspective view of the bottom stabilizer 108 of the incontinence clamping device 100, according to an exemplary embodiment of the present invention. In FIG. 5B, the second perspective view of the bottom stabilizer 106 has been shown from inside showing an inner surface. FIG. 5C is a diagram that illustrates a cross-sectional side view of the bottom stabilizer 108 of the incontinence clamping device 100, according to an exemplary embodiment of the present invention. In an embodiment, the bottom stabilizer 108 may be made up of a polycarbonate material.

In an embodiment, the bottom stabilizer 108 may comprise a lock 108a (provided on the outer surface) that is configured to get locked with the lock ring of the bottom clamp arm 104. In one embodiment, the lock 108a may be manually placed into the lock ring and then may be manually rotated in one direction (for example, in a clockwise direction) to complete the locking of the lock 108a with the lock ring of the bottom clamp arm 104. Similarly, to perform unlocking, the lock 108a may be manually rotated in the opposite direction (for example, in an anti-clockwise direction) to unlock the lock 108a from the lock ring of the bottom clamp arm 104. In another embodiment, the lock 108a may be a toggle lock and may include a mechanical button that can be operated to lock or unlock the lock 108a into or out of the lock ring of the bottom clamp arm 102.

In an embodiment, the bottom stabilizer 108 may further comprise the inner surface having a plurality of zig-zag portions (as shown by 108b and 108c) including one or more elevated portions 108b and non-elevated portions 108c. Further, the central elevated portion may include a circular gap or hole 108d. The elevated portions 108b and the non-elevated portions 108c may be adjacent to each other. Each of the elevated portions 108b or the non-elevated portions 108c may be square or rectangular in shape as shown. However, the central elevated portion is like a diamond or crown shaped portion having the circular gap or hole 108d at its center as shown. The bottom stabilizer 108 may further comprise an elevated portion 108e on its outer surface as shown.

Figure 6A:
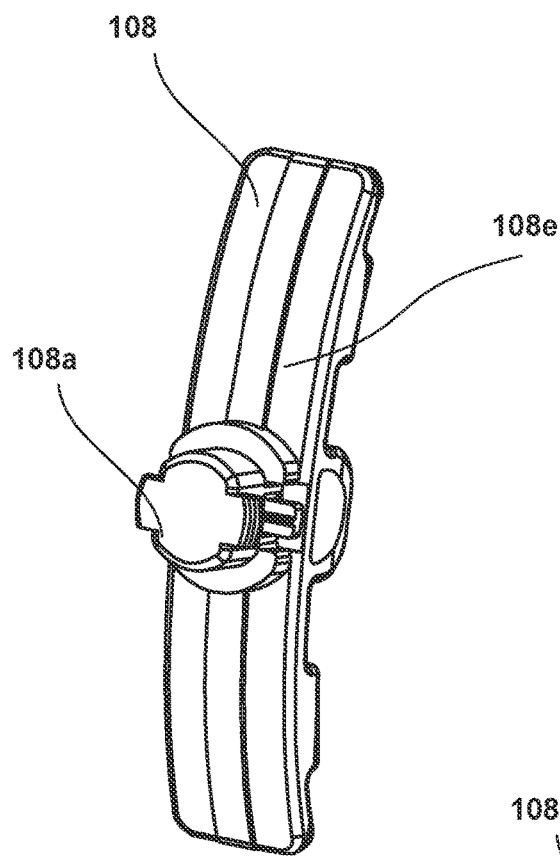
FIG. 6A is a diagram that illustrates a first perspective view of a bottom stabilizer of the incontinence clamping device, according to another exemplary embodiment of the present invention.
Figure 6C:
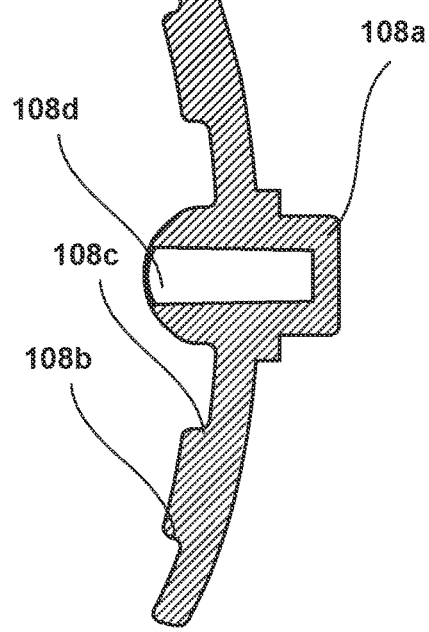
FIG. 6C is a diagram that illustrates a cross-sectional side view of the bottom stabilizer of the incontinence clamping device, according to another exemplary embodiment of the present invention.
Figure 6B:
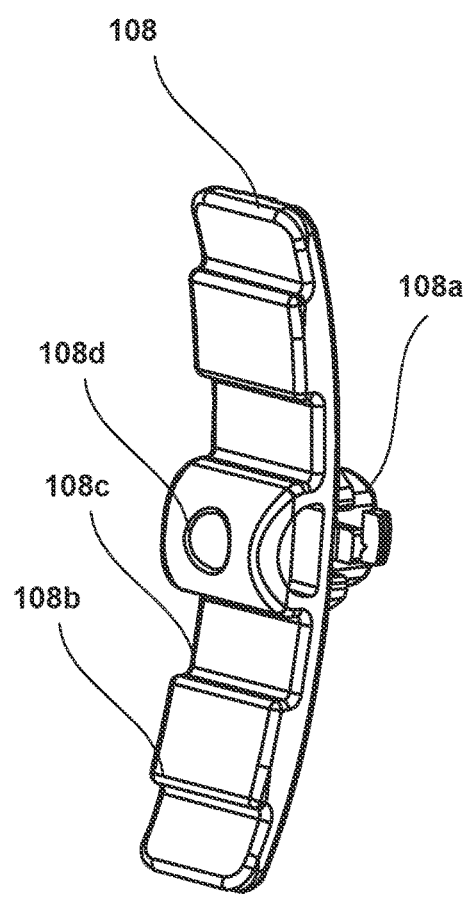
FIG. 6B is a diagram that illustrates a second perspective view of the bottom stabilizer of the incontinence clamping device, according to another exemplary embodiment of the present invention.

FIG. 6A is a diagram that illustrates a first perspective view of the bottom stabilizer 108 of the incontinence clamping device 100, according to another exemplary embodiment of the present invention. In FIG. 6A, the first perspective view of the bottom stabilizer 108 has been shown from outside showing an outer surface. FIG. 6B is a diagram that illustrates a second perspective view of the bottom stabilizer 108 of the incontinence clamping device 100, according to another exemplary embodiment of the present invention. In FIG. 6B, the second perspective view of the bottom stabilizer 106 has been shown from inside showing an inner surface. FIG. 6C is a diagram that illustrates a cross-sectional side view of the bottom stabilizer 108 of the incontinence clamping device 100, according to another exemplary embodiment of the present invention. The only difference in the bottom stabilizer 108 (of FIGS. 6A, 6B, and 6C) with respect to the bottom stabilizer 108 (of FIGS. 5A, 5B, and 5C) is that the bottom stabilizer 108 (of FIGS. 6A, 6B, and 6C) includes the central elevated portion that is like an oval shaped portion unlike the bottom stabilizer 108 (of FIGS. 5A, 5B, and 5C) that has the diamond or crown shaped portion.

Figures 7A, 7B:
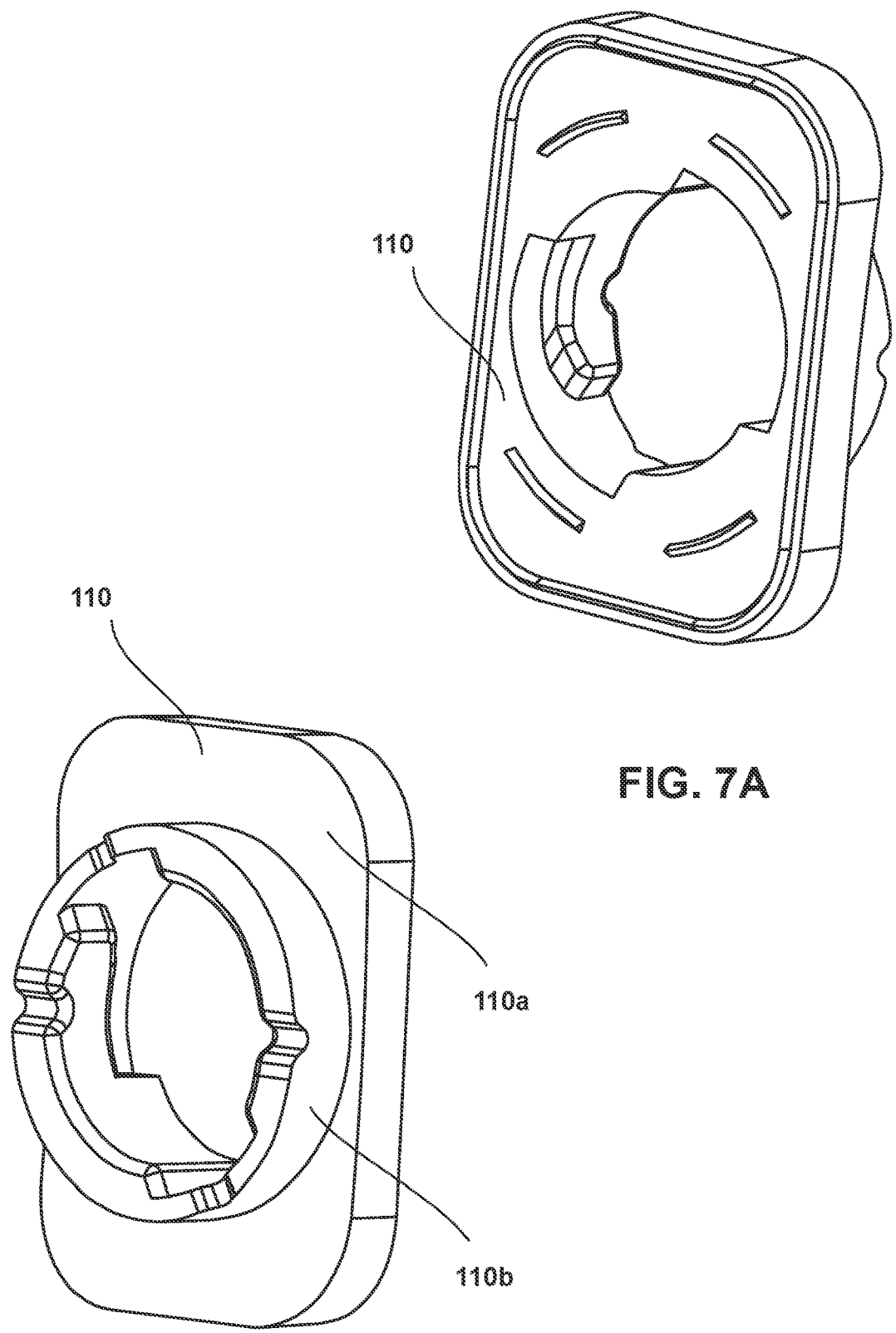
FIGS. 7A and 7B are diagrams that illustrate a perspective view of a lock ring of the incontinence clamping device, according to an exemplary embodiment of the present invention.

FIGS. 7A and 7B are diagrams that illustrate a perspective view of the lock ring 110 of the incontinence clamping device 100, according to an exemplary embodiment of the present invention. In an embodiment, the lock ring 110 is made up of a polycarbonate material.

In one embodiment, the lock ring 110 fits into the locking segment 102c from inside of the upper clamp arm 102. Further, the top stabilizer 106 may be configured to get locked with the lock ring 110 of the upper clamp arm 102. Here, for example, the lock 106a may be manually placed into the lock ring 110 of the upper clamp arm 102 and then may be manually rotated in one direction (for example, in a clockwise direction) to complete the locking of the lock 106a with the lock ring 110 of the upper clamp arm 102. Further, another lock ring 110 fits into the locking segment 104c from inside of the bottom clamp arm 104. The bottom stabilizer 108 may be configured to get locked with the lock ring 110 of the bottom clamp arm 104. Here, for example, the lock 108a may be manually placed into the lock ring 110 of the bottom clamp arm 104 and then may be manually rotated in one direction (for example, in a clockwise direction) to complete the locking of the lock 108a with the lock ring 110 of the bottom clamp arm 104.

In an embodiment, the lock ring 110 includes a flat surface 110a and a protruded portion 110b. The flat surface 110a has two sides, say a first side and a second side. The protruded portion 110b is like a hollow cylindrical such that there is circular gap in the lock ring 110. Further, the first side of the flat surface fits into the locking segment 102c or 104c from inside of the upper or bottom clamp arm 102 or 104. Further, the top or bottom stabilizer 106 or 108 may fit into the protruded portion 110 b on the second surface of the lock ring 110 of the upper or bottom clamp arm 102 or 104.

Figure 8A:
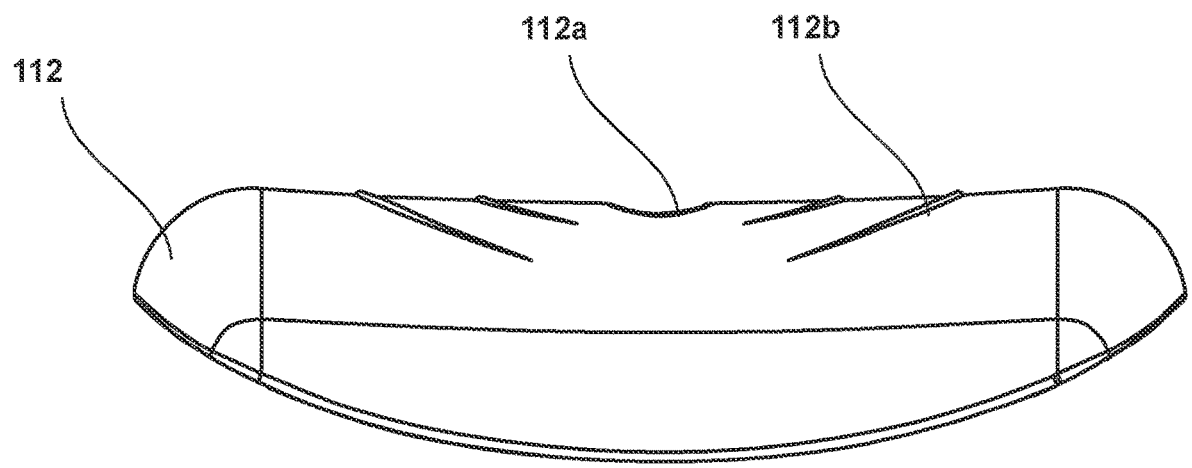
FIG. 8A is a diagram that illustrate a side view of an upper silicone fitting of the incontinence clamping device, according to an exemplary embodiment of the present invention.

FIG. 8A is a diagram that illustrate a side view of an upper silicone fitting 112 of the incontinence clamping device 100, according to an exemplary embodiment of the present invention. The upper silicone fitting 112 has two surfaces, say a lower portion that is semi-circular in shape and an upper portion that is a flat surface. The upper portion may include a protrusion (e.g., a bump) 112a that is facing inward. The upper portion may further include one or more linings 112b that are uniformly distributed on both sides of the protrusion 112a. Further, the lower portion may include a circular hole or gap that is located at its center.

Figure 8B:
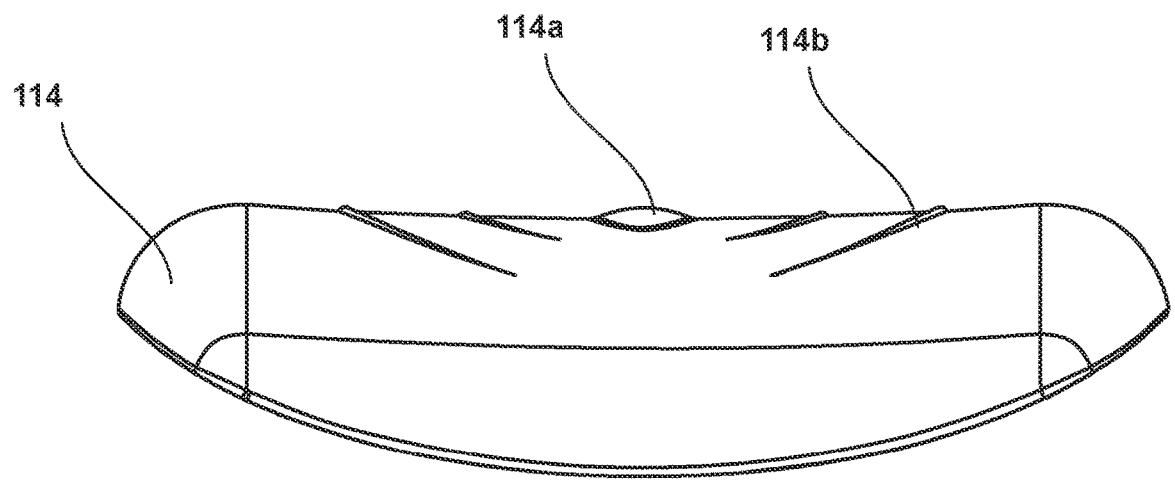
FIG. 8B is a diagram that illustrates a side view of a bottom silicone fitting of the incontinence clamping device, according to an exemplary embodiment of the present invention.

FIG. 8B is a diagram that illustrates a side view of a bottom silicone fitting 114 of the incontinence clamping device 100, according to an exemplary embodiment of the present invention. The bottom silicone fitting 114 has two surfaces, say a lower portion that is semi-circular in shape and an upper portion that is a flat surface. The upper portion may include a protrusion (e.g., a bump) 114a that is facing outward. The upper portion may further include one or more linings 114b that are uniformly distributed on both sides of the protrusion 114a. Further, the lower portion may include a circular hole or gap that is located at its center.

Figure 9:
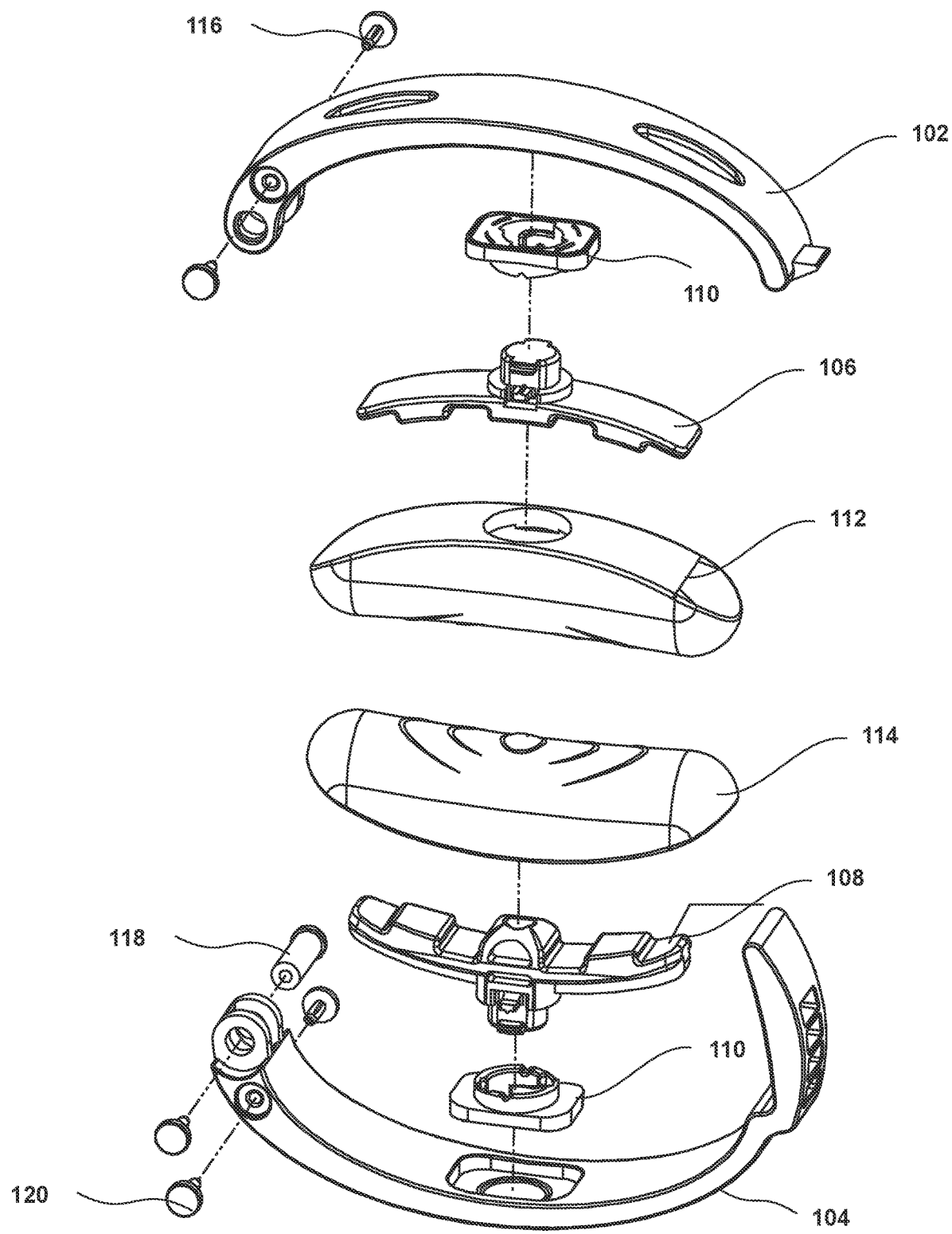
FIG. 9 is a diagram that illustrates a distributed arrangement of all components of the incontinence clamping device, according to an exemplary embodiment of the present invention.

FIG. 9 is a diagram that illustrates a distributed arrangement of all components of the incontinence clamping device 100, according to an exemplary embodiment of the present invention. The incontinence clamping device 100 includes the upper clamp arm 102, the bottom clamp arm 104, the top stabilizer 106, the bottom stabilizer 108, the lock ring 110, the upper silicone fitting 112, and the bottom silicone fitting 114. The upper lock ring 110 fits into the upper clamp arm 102. Further, the top stabilizer 106 is locked into the upper lock ring 110. The top stabilizer 106 is further fitted into the upper silicone fitting 112. Similarly, the bottom lock ring 110 fits into the bottom damp arm 104. Further, the bottom stabilizer 108 is locked into the bottom lock ring 110. The bottom stabilizer 108 is further fitted into the bottom silicone fitting 114. Further, the upper clamp arm 102 and the bottom clamp arm 104 are attached to each other by means of one or more plastic plugs such as nut-bolt assemblies (as shown by 116, 118, and 120).

Figure 10:
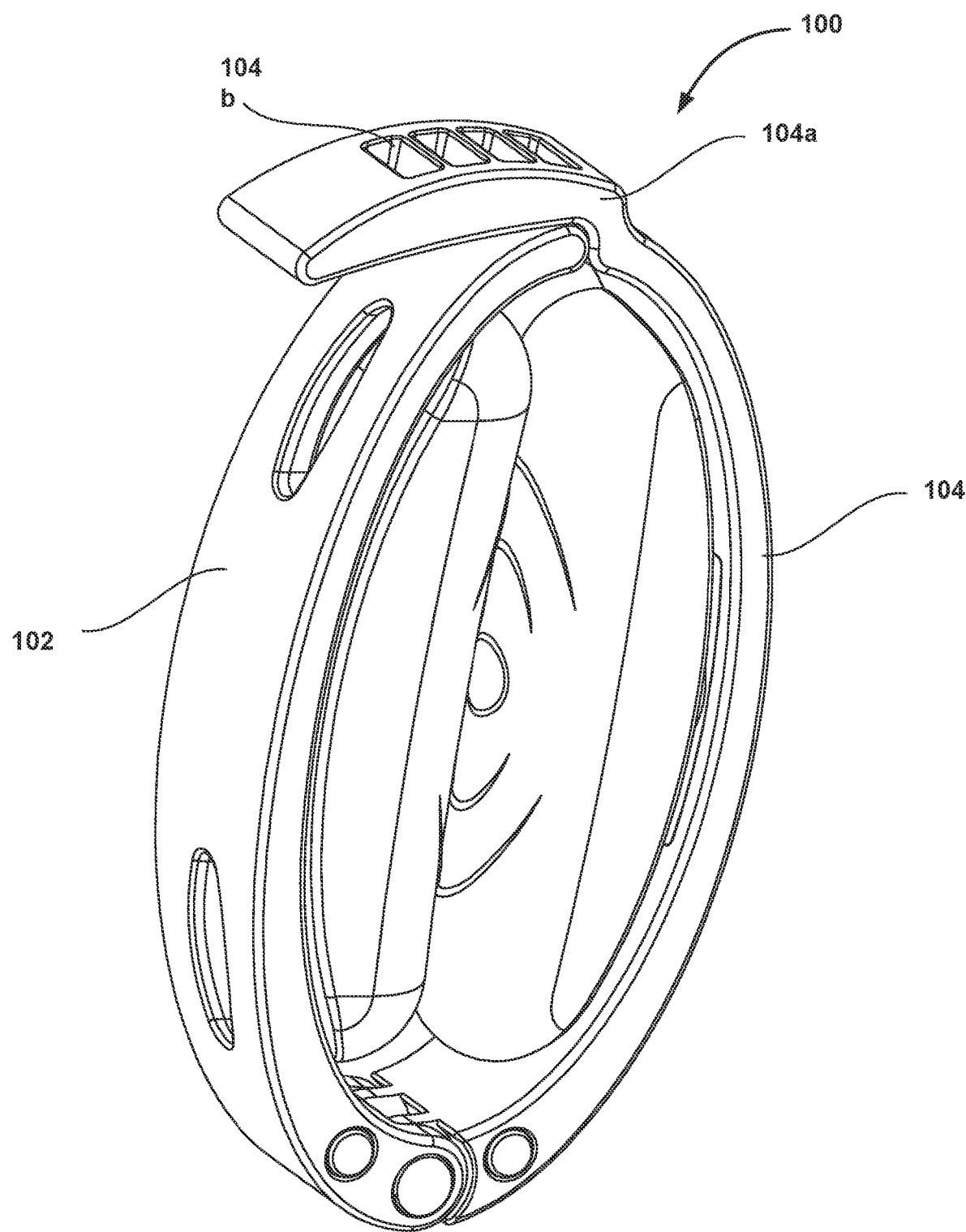
FIG. 10 is a diagram that illustrates a perspective view of the incontinence clamping device in a closed state, according to an exemplary embodiment of the present invention.
Figure 11:
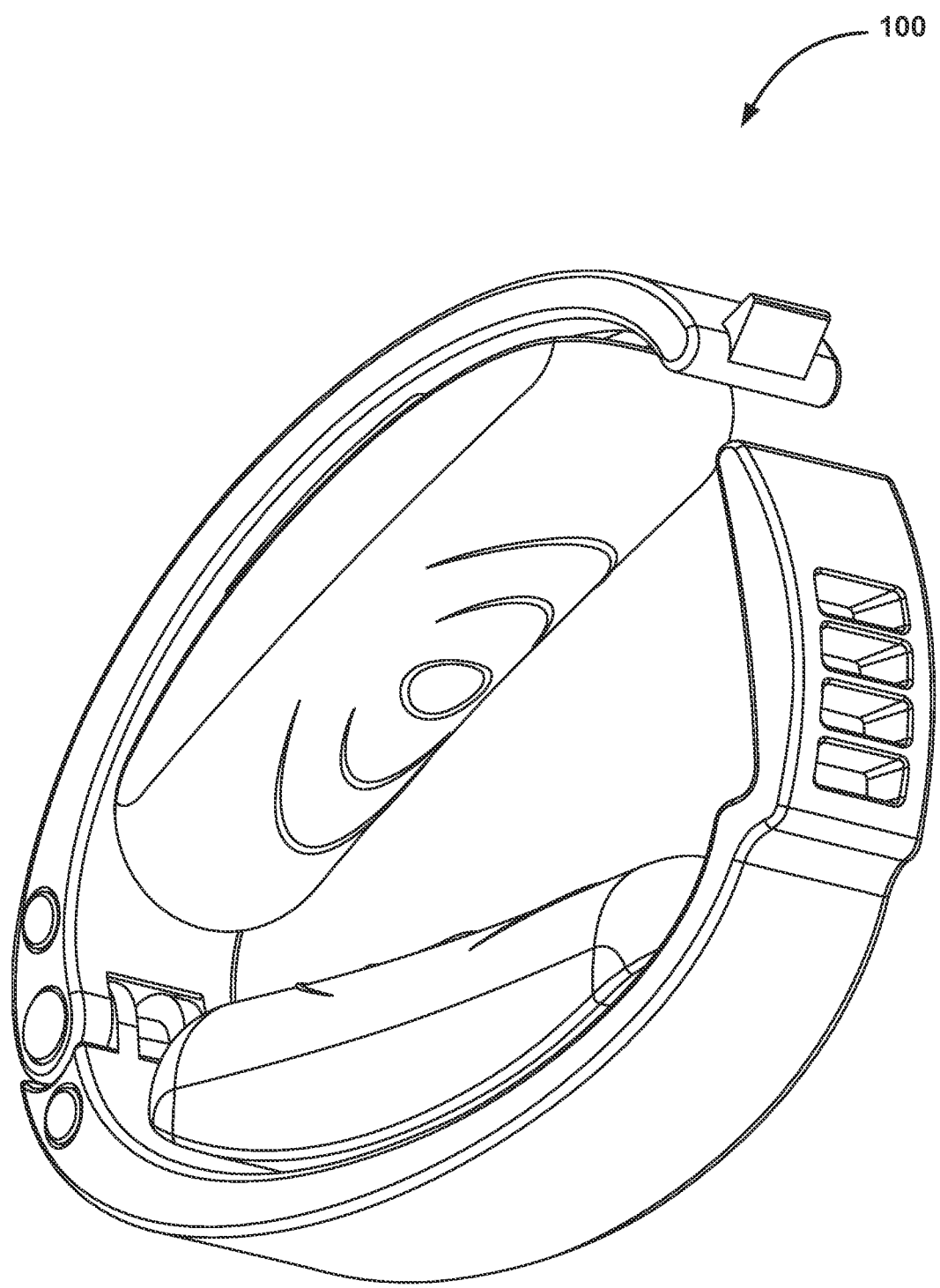
FIG. 11 is a diagram that illustrates a perspective view of the incontinence clamping device in an open state, according to an exemplary embodiment of the present invention.
Figure 12:
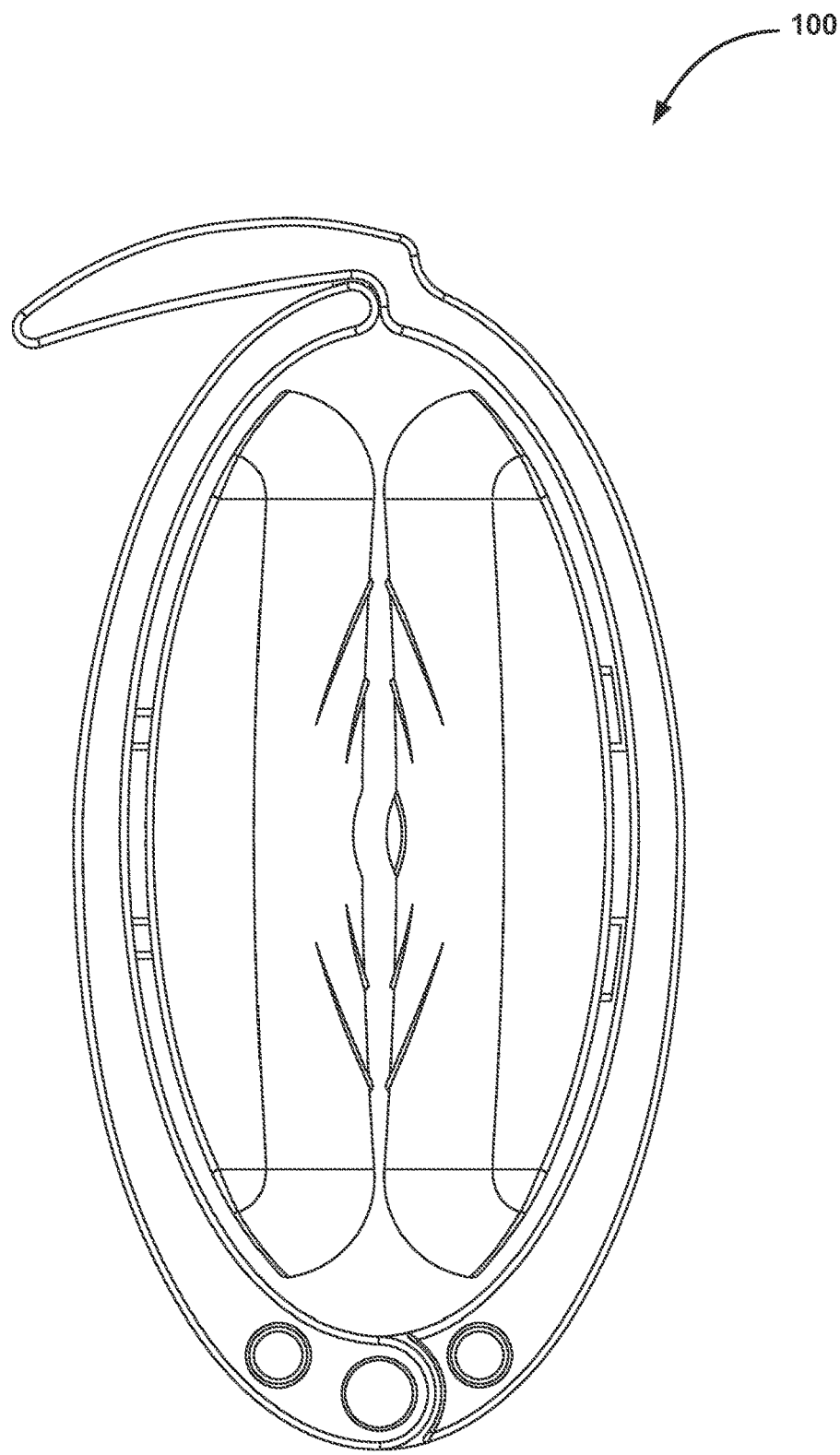
FIG. 12 is a diagram that illustrates a side view of the incontinence clamping device in its closed state, according to an exemplary embodiment of the present invention.

FIG. 10 is a diagram that illustrates a perspective view of the incontinence damping device 100 in a closed state, according to an exemplary embodiment of the present invention. Here it is shown that the upper clamp arm 102 is removably attached to the bottom clamp arm 104 by means of the stopper 102a and the device locking component 104a. In an embodiment, the stopper 102a is inserted into one of the pluralities of interlocking gaps 104b to establish the locking of the upper clamp arm 102 with the bottom clamp arm 104. FIG. 11 is a diagram that illustrates a perspective view of the incontinence clamping device 100 in an open state, according to an exemplary embodiment of the present invention. In the open state, the upper clamp arm 102 is not attached to the bottom clamp arm 104 i.e., the stopper 102a is not inserted into any of the plurality of interlocking gaps 104b. FIG. 12 is a diagram that illustrates a side view of the incontinence clamping device 100 in its closed state, according to an exemplary embodiment of the present invention.

Figure 13:
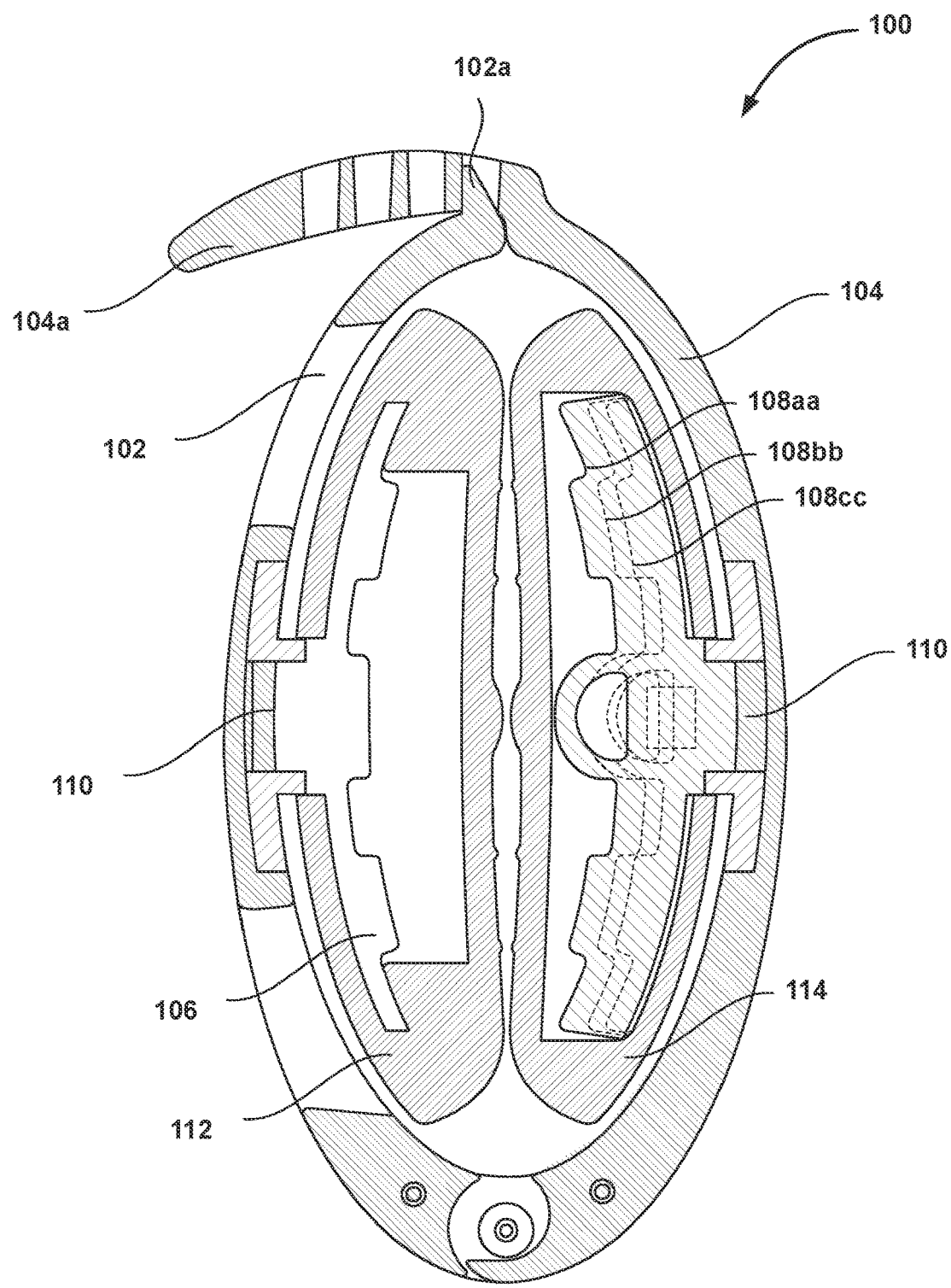
FIG. 13 is a diagram that illustrates a cross-sectional side view of the incontinence clamping device in its closed state, according to an exemplary embodiment of the present invention.

FIG. 13 is a diagram that illustrates a cross-sectional side view of the incontinence clamping device 100 in its closed state, according to an exemplary embodiment of the present invention. As shown, the top stabilizer 106 is attached to the lock ring 110. Similarly, the bottom stabilizer 108aa is attached to the lock ring 110. Alternatively, depending on the user's preferences such as the user's penis size, other variants of the bottom stabilizer 108bb or 108cc may be attached to the lock ring 110. These variants of the bottom stabilizer 108bb or 108cc may have a size that is different (smaller or larger) than the size of bottom stabilizer 108aa. Further, the top stabilizer 106 is inserted into the upper silicone fitting 112 as shown herein. Similarly, the bottom stabilizer 108aa, 108bb, or 108cc may be inserted into the bottom silicone fitting 114 as shown. Further, the upper clamp arm 102 is locked with the bottom clamp arm 104 by means of the stopper 102a and the device locking component 104a. In an embodiment, the stopper 102a is inserted into one of the pluralities of interlocking gaps 104b to establish the locking of the upper clamp arm 102 with the bottom clamp arm 104.

One embodiment of the incontinence clamping device 100 can include a hinge 200 different from that shown in FIGS. 1-13. With reference to FIGS. 14-23, the device 100 can include an adjustable hinge 200 to rotatably connect the upper clamp arm 102 and the bottom clamp arm 104 together. The adjustable hinge 200 can be comprised from several components, including an upper clamp arm 102 with an elongated ovular opening 202 defined therein, a bottom clamp arm 104 with a circular opening 204 defined therein, and a hinge pin 210 disposed within the openings 202 and 204.

Figure 14:
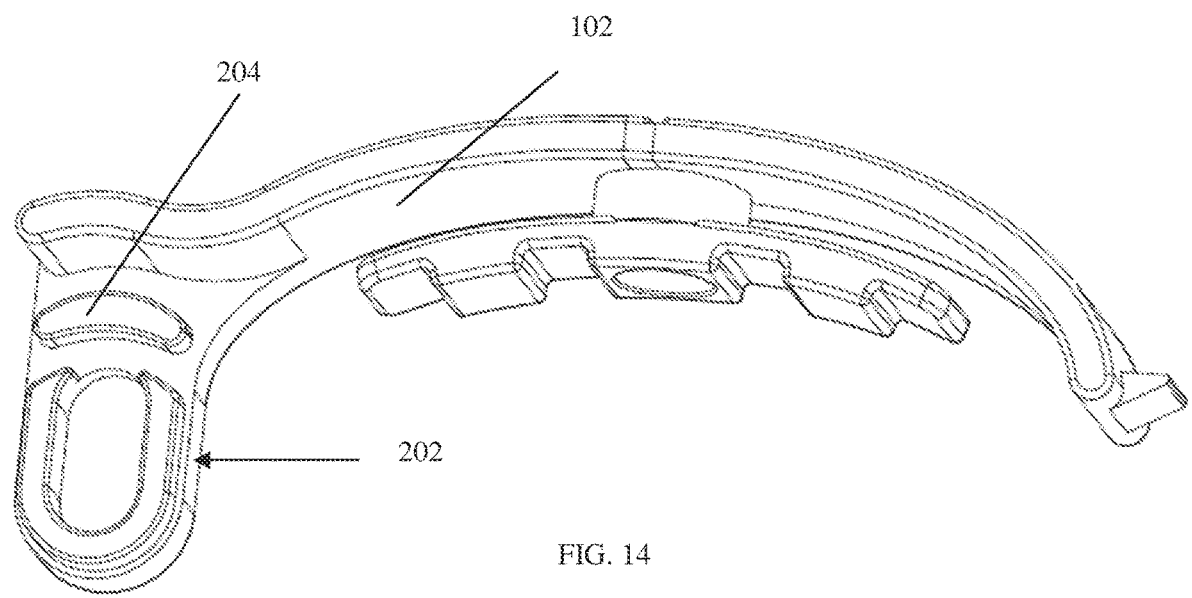
FIG. 14 is a diagram that illustrates a perspective view of an embodiment of an upper clamp arm of the incontinence clamping device.
Figure 15:
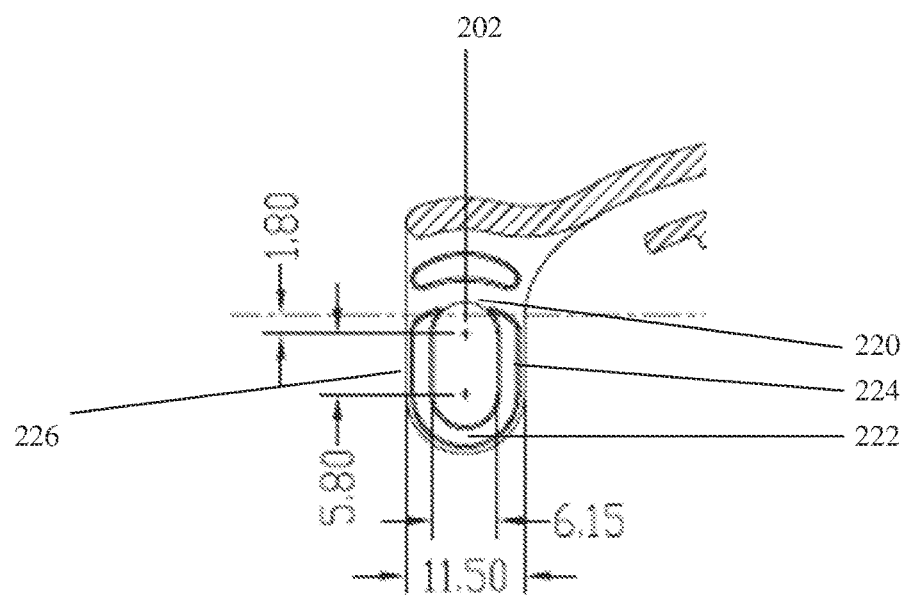
FIG. 15 is a diagram that illustrates a partial front view of an embodiment of an upper clamp arm of the incontinence clamping device.

With specific reference to FIG. 14 and FIG. 15, the upper clamp arm 102 can define the elongated opening 202 and include a raised shoulder 204. The purpose of the raised shoulder 204 will be discussed in more detail below with reference to FIG. 22 and FIG. 23. The upper clamp arm 102 can further include a shoulder surrounding a majority of the perimeter of the elongated opening, to help retain the hinge pin 210 therein.

As shown in FIG. 15, the elongated opening 202 is defined by two annular sides 220, 222 and two linear sides 224, 226. The elongated opening has a width, defined as the distance between the first linear side and the second linear side. In an embodiment, the width of the elongated opening 202 can be approximately 6.15 millimeters. The elongated opening can have, but need not have, other specific geometry and measurements, including those shown in FIG. 15, in millimeters.

Figure 16:
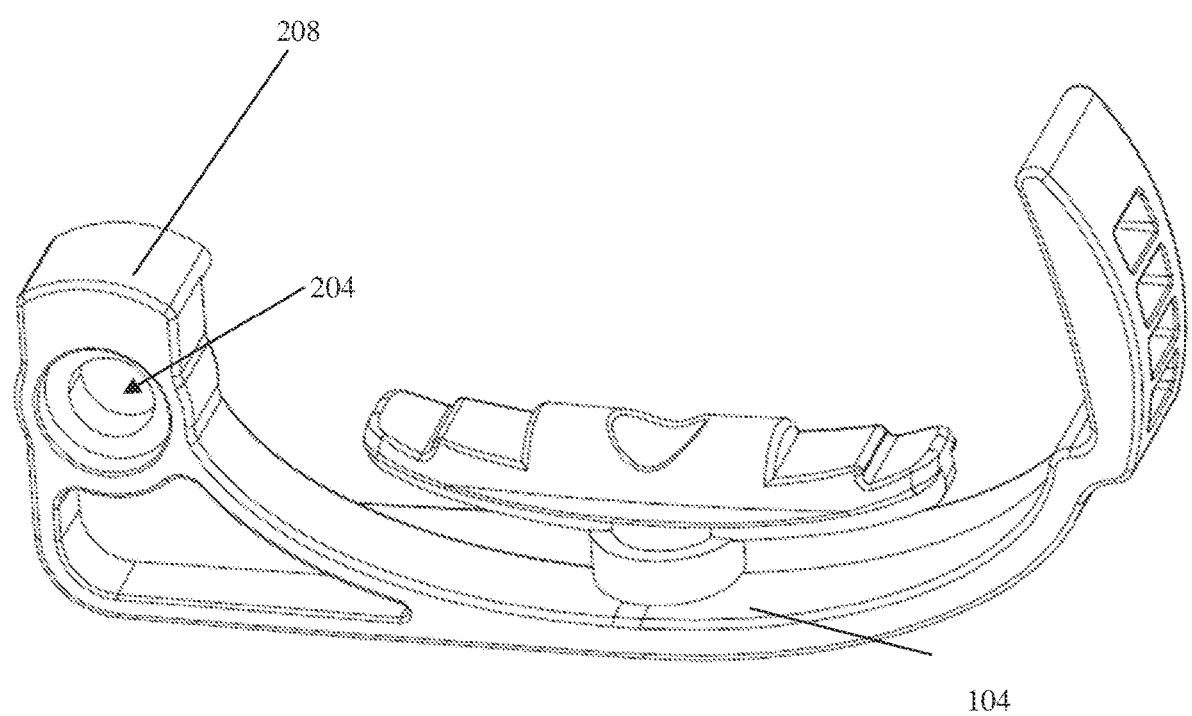
FIG. 16 is a diagram that illustrates a perspective view of an embodiment of a bottom clamp arm of the incontinence clamping device.

As shown in FIG. 16, the bottom clamp arm 104 can define a generally circular opening 206. In an embodiment, the circular opening has a diameter, and, in an embodiment, the diameter is approximately 6.15 millimeters. The bottom clamp arm 104 can also include a leading edge 208, the purpose of which will be discussed in more detail below with reference to FIG. 22 and FIG. 23 below.

Figure 17:
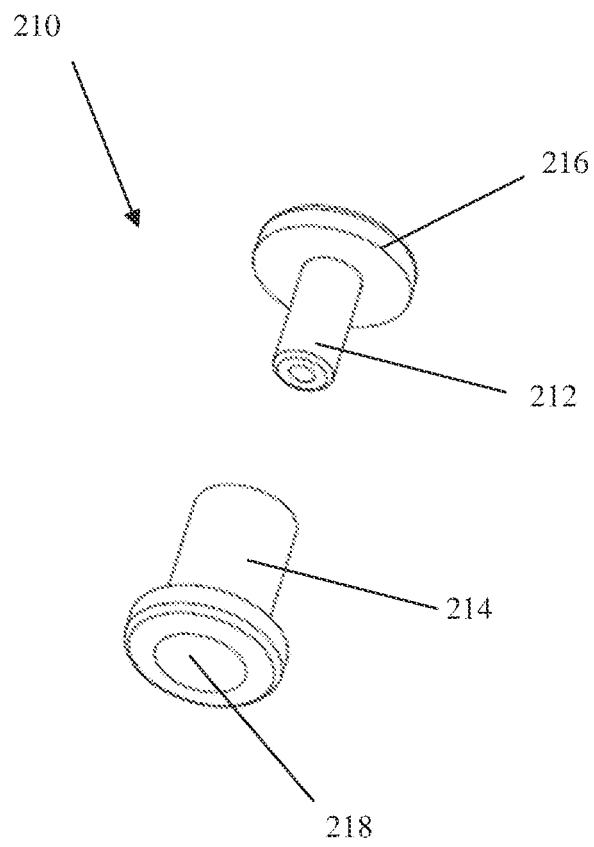
FIG. 17 is a diagram that illustrates a perspective view of an embodiment of a hinge pin of the incontinence clamping device.

As shown in FIG. 17, the hinge pin 210 may be comprised of two cylinders, a first cylinder 212 and a second cylinder 214. The outer diameter of the first cylinder 212 is configured to be less than the inner diameter of the second cylinder 214, such that the first cylinder 212 can be telescopically inserted into the second cylinder, to form a coupled hinge pin having two circular stops 216, 218 and a combined cylindrical shaft coupled between the two circular stops. The outer diameters of the first cylinder 212 and second cylinder 214 are both configured to be less than the diameter of the circular opening 204 and width of the elongated opening 202 (e.g. both less than 6.15 millimeters). In an embodiment, the outer diameter of the first cylinder 212 is 3.5 millimeters and the outer diameter of the second cylinder 214 is 6.0 millimeters. The stops 216, 218 can be circular and have diameters larger than the diameter of the circular opening and larger than the width of the elongated ovular opening. In an embodiment, the circular stops are larger than 6.15 millimeters, and, in one specific embodiment, one or both of the circular stops have a diameter of approximately 9.2 millimeters.

In operation, the hinge pin 210 will be fixably and rotatably retained within the circular opening 204 of the bottom clamp arm 104, but will be able to translate within the elongated opening 202 of the upper clamp arm 102. One will appreciate that, in an embodiment not shown, the circular opening may be defined within the upper clamp arm 102 and the elongated opening 202 may be defined in the bottom clamp arm 104.

Figure 18:
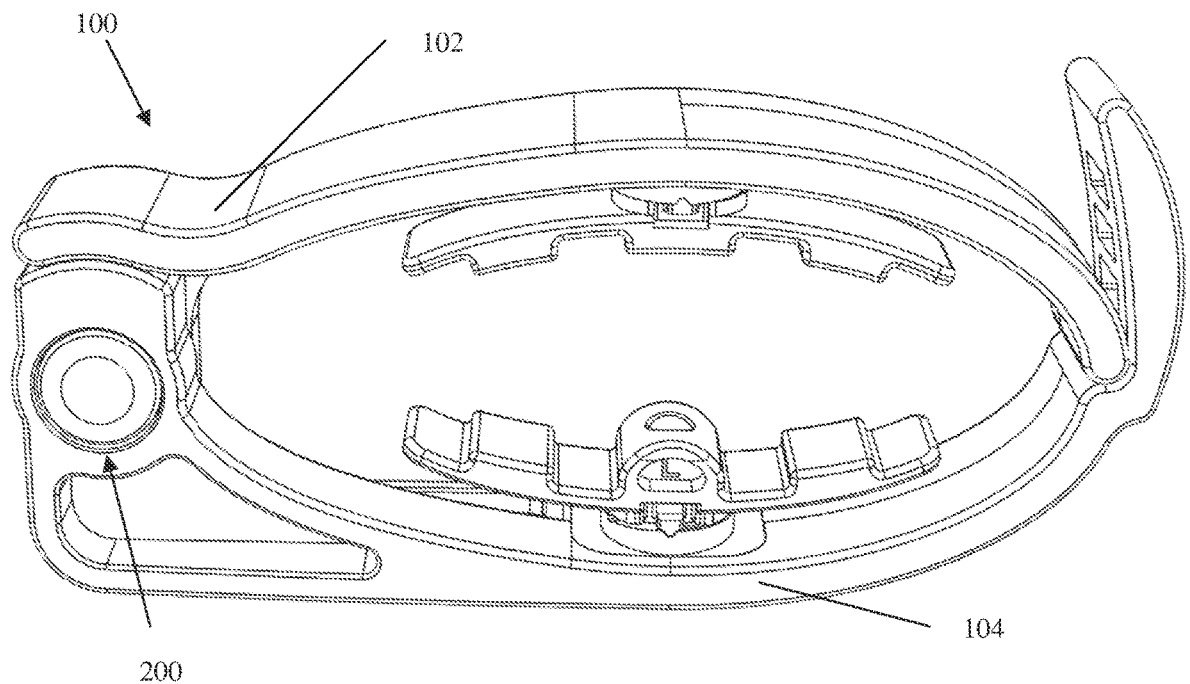
FIG. 18 is a diagram that illustrates a perspective front view of incontinence clamping device in a first mode.
Figure 19:
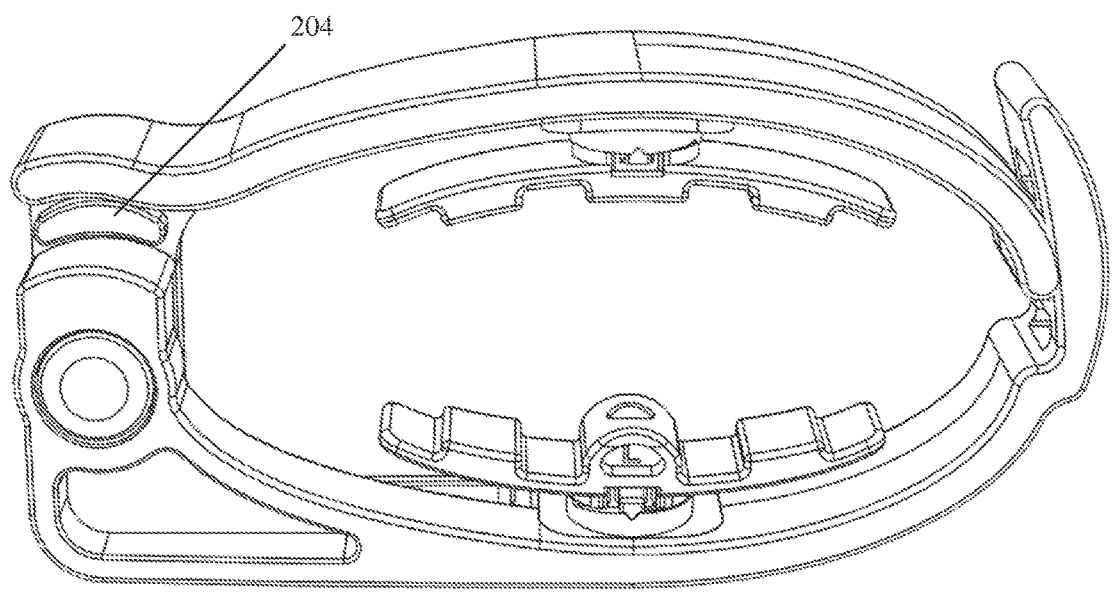
FIG. 19 is a diagram that illustrates a perspective front view of incontinence clamping device in a second mode.
Figure 20:
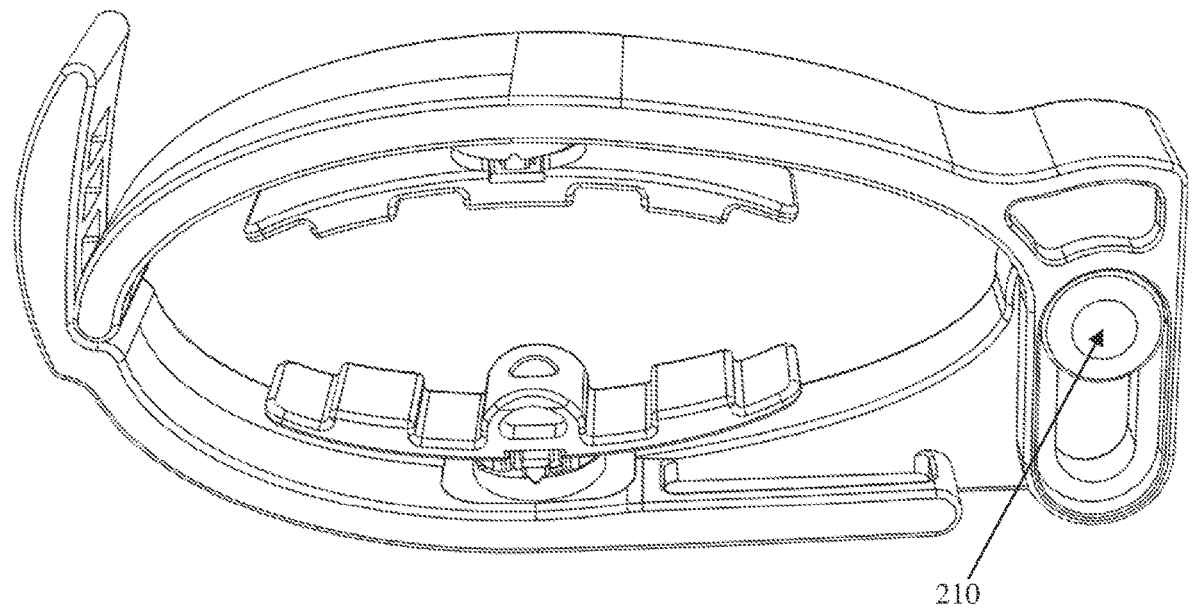
FIG. 20 is a diagram that illustrates a perspective rear view of incontinence clamping device in a first mode.
Figure 21:
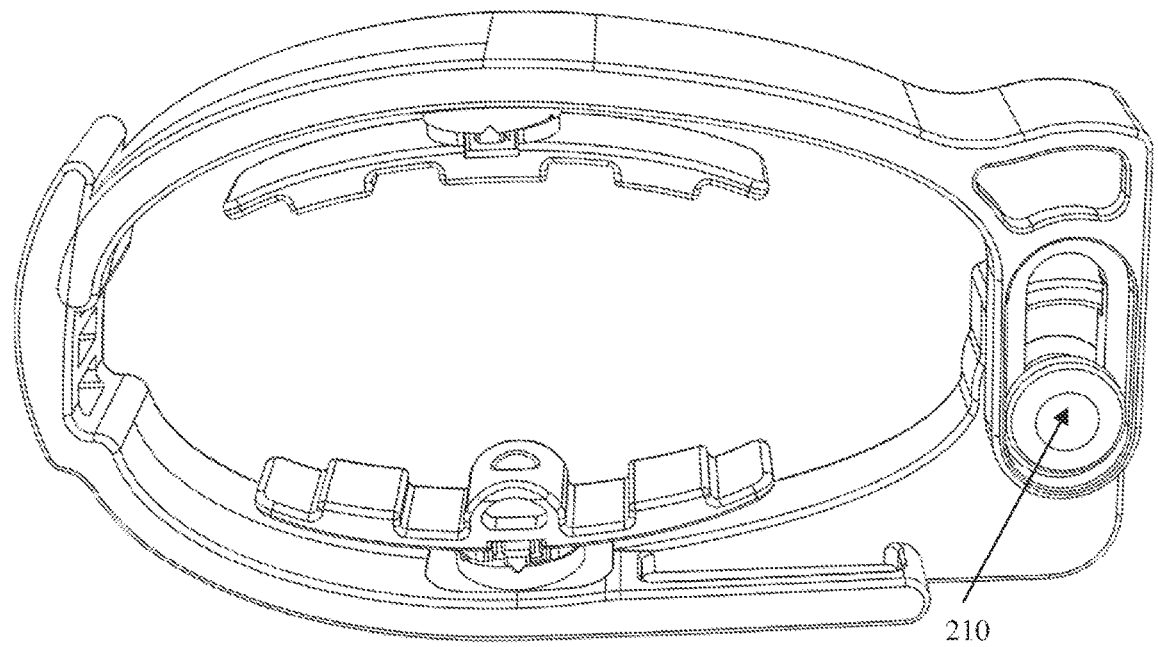
FIG. 21 is a diagram that illustrates a perspective rear view of incontinence clamping device in a second mode.

With reference to FIGS. 18-21, when assembled, the device 100 can be configured into one of two modes, either in the first mode of FIGS. 18 and 20, or in the second mode of FIGS. 19 and 21. As can be seen by comparison of the figures, the second mode provides a greater distance between the upper clamp arm 102 and the bottom clamp arm 104, to help facilitate different user preference of size and pressure. In this way, the hinge 200 provides another degree of adjustability to the incontinence clamp device 100 that would not otherwise be available.

As shown in the first mode, and in FIG. 18 specifically, the bottom clamp arm 104 is snugly positioned adjacent to the upper clamp arm 102, and the raised shoulder 204 is not visible to the user. On the reverse view shown in FIG. 20, the hinge pin 210 is disposed towards the upper end of the elongated opening 202. As shown in the second mode, and in FIG. 19 specifically, the bottom clamp arm 104 is positioned a greater distance away from the upper clamp arm 102, and the raised shoulder 204 is visible to the user. On the reverse view shown in FIG. 21, the hinge pin 210 has been translated downward as illustrated and is disposed towards the bottom end of the elongated opening 202.

To facilitate proper positioning between the two modes shown and described, the upper clamp arm 102 may also include a raised shoulder 204 that cooperates with the leading edge 208 of the bottom clamp arm 104. As shown in FIGS. 22 and 22, when a user desires to change between the first mode and the second mode, the user will rotate the bottom clamp arm 104 clockwise about the hinge pin 210, while translating the hinge pin 210 within the elongated slot 202. When the user has selected his desired mode, he will rotate the bottom clamp arm 104 counterclockwise about the hinge pin 210. The amount that the user translates the hinge pin 210 within the elongated slot 202 will determine whether the counterclockwise rotation will result in the first mode (FIG. 23) or second mode (FIG. 22). If the hinge pin 210 is disposed between the two extremes of the elongated slot 202 when the user rotates counterclockwise, the rounded entry profile of raised shoulder 204 will direct the leading edge 208 down one of the two available paths 230, 232, thereby setting the device in one of the two available modes. The interference interaction between the raised edge 204 and leading edge 208 when in one of the two possible modes prevents further translation of the hinge pin 210 within the elongated slot 202; a user must substantially rotate the arm to remove the interference and permit translation.

The adjustable hinge 200 shown and described herein allows users to resize the incontinence clamping device 100 or modify the pressure exhibited by the device. As a result, the adjustable hinge 200 provides a better user experience. The hinge 200 may be utilized alone or in combination with other features (e.g. using the stopper 102a to secure the end opposite from the hinge), to provide the user with a secure, comfortable, and adjustable device that fits their needs and preferences.

Embodiments described herein may be combined in a novel and inventive way to provide advantages that were not previously observed in the art. This disclosure should not necessarily be interpreted to be limited to only the embodiments shown and described, as embodiments described may appear differently than as shown, and drawings shown may be understood differently than as described.

What is claimed is:

1. An incontinence clamping device comprising an adjustable hinge, the adjustable hinge comprising:
   an upper clamp arm defining an elongated slot, the elongated slot having a first end and a second end:
   a lower clamp arm defining a circular opening;
   a hinge pin disposed within the elongated slot and sized to retainably translate within the elongated slot, the hinge pin also disposed within the circular opening and sized to retainably rotate within the lower clamp arm,
   wherein the incontinence clamp device comprises a first mode and a second mode, the first mode comprising the hinge pin translated to the first end of the elongated slot, and the second mode comprising the hinge pin translated to the second end of the elongated slot,
   wherein the upper clamp arm further comprises a raised shoulder;
   wherein the lower clamp arm comprises a leading edge, and
   wherein the raised shoulder and the leading edge interfere with one another to prohibit translation of the hinge pin within the elongated slot unless the lower clamp arm comprising the leading edge is rotated about the hinge pin, with the leading edge rotated to pass around the raised shoulder.

2. The incontinence clamping device of claim 1, wherein the raised shoulder is configured to direct the leading edge along one of two possible paths.

3. The incontinence clamping device of claim 1, wherein the width of the elongated slot and the diameter of the circular opening are approximately 6.15 millimeters.

4. The incontinence clamping device of claim 1, wherein the hinge pin comprises a first cylindrical shaft, a second cylindrical shaft telescopically disposed within the first cylindrical shaft, a circular stop coupled to the first cylindrical shaft, and a second circular stop coupled to the second cylindrical shaft.

5. The incontinence clamping device of claim 1, wherein the lower clamp arm must be rotated about the hinge pin clockwise and then counterclockwise to transition between the first mode and the second mode.

* * * * *